US011760965B2

(12) United States Patent
Jackson-Holmes et al.

(10) Patent No.: US 11,760,965 B2
(45) Date of Patent: Sep. 19, 2023

(54) MESOFLUIDIC DEVICE FOR CULTURE OF CELL AGGREGATES

(71) Applicants: Georgia Tech Research Corporation, Atlanta, GA (US); Emory University, Atlanta, GA (US)

(72) Inventors: Emily Jackson-Holmes, Atlanta, GA (US); Hang Lu, Atlanta, GA (US); Zhexing Wen, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 538 days.

(21) Appl. No.: 16/755,915

(22) PCT Filed: Oct. 19, 2018

(86) PCT No.: PCT/US2018/056720
§ 371 (c)(1),
(2) Date: Apr. 14, 2020

(87) PCT Pub. No.: WO2019/079725
PCT Pub. Date: Apr. 25, 2019

(65) Prior Publication Data
US 2020/0318045 A1    Oct. 8, 2020

Related U.S. Application Data

(60) Provisional application No. 62/574,293, filed on Oct. 19, 2017.

(51) Int. Cl.
*C12M 1/00*    (2006.01)
*B01L 3/00*    (2006.01)

(52) U.S. Cl.
CPC .............. *C12M 23/02* (2013.01); *B01L 3/502* (2013.01); *B01L 2200/0668* (2013.01);
(Continued)

(58) Field of Classification Search
None
See application file for complete search history.

(56) References Cited

U.S. PATENT DOCUMENTS 9,267,103 B2   2/2016  Lichtenberg et al.
9,701,938 B2   7/2017  Vukasinovic
(Continued)

FOREIGN PATENT DOCUMENTS

WO   2012/014047   2/2012
WO   2013126774    8/2013
WO   2017/027838   2/2017

OTHER PUBLICATIONS

Search Report and Written Opinion from PCT application No. PCT/US18/056720 dated Feb. 19, 2019.
(Continued)

*Primary Examiner* — Lore R Jarrett
(74) *Attorney, Agent, or Firm* — Troutman Pepper Hamilton Sanders LLP; Ryan A. Schneider; Brandon M. Reed

(57) ABSTRACT

Mesofluidic devices for culturing cell aggregates and methods of using the same are disclosed. An exemplary mesofluidic device comprises at least one fluid inlet, at least one fluid outlet, a plurality of fluid channels, and a plurality of culture chambers. Each culture chamber can comprise at least one chamber inlet and at least one chamber outlet. The at least one chamber inlet can be in fluid communication with the at least one fluid inlet via at least one of the plurality of fluid channels. The at least one chamber outlet can be in fluid communication with the at least one fluid outlet via at least one of the plurality of fluid channels. The mesofluidic device can be configured to contain a cell aggregate in each of the plurality of culture chambers.

7 Claims, 21 Drawing Sheets

(52) U.S. Cl.
CPC . *B01L 2300/087* (2013.01); *B01L 2300/0883* (2013.01); *B01L 2400/084* (2013.01)

(56) References Cited

U.S. PATENT DOCUMENTS

| | | | |
|---|---|---|---|
| 9,790,465 | B2 | 10/2017 | Bennett et al. |
| 9,931,629 | B2 | 4/2018 | Cooper-White et al. |
| 10,232,371 | B2 | 3/2019 | Collins |
| 10,351,819 | B2 | 7/2019 | Hribar et al. |
| 10,532,355 | B2 | 1/2020 | Trietsch et al. |
| 2003/0199081 | A1* | 10/2003 | Wilding ............... C12Q 1/686 435/287.2 |
| 2004/0067482 | A1* | 4/2004 | Yasuda ................ C12M 41/36 435/287.1 |
| 2009/0042736 | A1 | 2/2009 | Bomer et al. |
| 2011/0262906 | A1* | 10/2011 | Dimov ............... B01L 3/50273 435/7.1 |
| 2011/0269226 | A1 | 11/2011 | Van Noort et al. |
| 2012/0009671 | A1* | 1/2012 | Hansen ................ C12M 23/16 435/325 |
| 2013/0078163 | A1 | 3/2013 | Chung et al. |
| 2014/0363838 | A1 | 12/2014 | McDevitt et al. |
| 2014/0363883 | A1 | 12/2014 | Hayes et al. |
| 2015/0004686 | A1 | 1/2015 | Goral et al. |
| 2015/0166956 | A1* | 6/2015 | Puleo ............... B01D 21/2444 435/2 |
| 2015/0240194 | A1 | 8/2015 | Neumann et al. |
| 2015/0369721 | A1 | 12/2015 | Deutsch et al. |
| 2016/0097028 | A1 | 4/2016 | Tung et al. |
| 2016/0252495 | A1 | 9/2016 | Ricicova et al. |
| 2016/0326477 | A1 | 11/2016 | Fernandez-Alcon et al. |
| 2016/0333298 | A1 | 11/2016 | Hung et al. |
| 2016/0340631 | A1 | 11/2016 | Wang et al. |
| 2017/0198245 | A1 | 7/2017 | Oh et al. |
| 2017/0283766 | A1 | 10/2017 | Hribar et al. |
| 2017/0342363 | A1 | 11/2017 | Fang et al. |
| 2018/0001231 | A1* | 1/2018 | Puleo ............... B01D 21/0006 |
| 2018/0085750 | A1 | 3/2018 | Varghese et al. |
| 2018/0187136 | A1 | 7/2018 | Lichtenberg et al. |
| 2020/0063081 | A1 | 2/2020 | Vulto et al. |

OTHER PUBLICATIONS

Khalili, et al., "A Microfluidic Device for Hydrodynamic Trapping and Manipulation Platform of a Single Biological Cell," Appl. Sci., 2016 vol. 6, No. 4 (17 pages).

* cited by examiner

MESOFLUIDIC DEVICE FOR CULTURE OF CELL AGGREGATES

CROSS-REFERENCE TO RELATED APPLICATIONS

This Application claims priority to U.S. Provisional Patent Application No. 62/574,293, filed 19 Oct. 2017, which is hereby incorporated by reference herein in its entirety as if fully set forth below.

STATEMENT OF RIGHTS UNDER FEDERALLY SPONSORED RESEARCH

This invention was made with government support under Grant No. CBET-0939511 awarded by the National Science Foundation. The government has certain rights in the invention.

FIELD OF THE DISCLOSURE

Embodiments of the present disclosure relate generally to mesofluidic devices and methods of using mesofluidic devices, and, more particularly, to mesofluidic devices and methods of using mesofluidic devices for culturing cell aggregates.

BACKGROUND

Cell aggregates can be artificially created to provide in vitro models for various tissues. For example, pluripotent stem cells (PSCs) are used in tissue engineering and biological studies because of their ability to differentiate into other types of cells. One common method of studying tissues involves creating three-dimensional structures of PSCs, or in other words, creating cell aggregates of PSCs. Aggregated PSCs can form complex tissue models, known as organoids, that provide researchers the ability to study models of tissue under varying biological environments and stresses. Organoids are valuable because of their ability to mimic any number of tissue structures, such as brain, liver, heart, gut, or any other tissue.

Necessarily, the size of an organoid or other cell aggregate depends greatly on parameters such as the starting number of cells, the type of cells being aggregated, and the length of time the organoid or aggregate is grown. Typical organoids used for tissue models can be very large on the biological scale—ranging from about 100 microns to a few millimeters in size. This places organoids, and other large cell aggregates, in a middle-range on the biological scale. When users culture an organoid or other large cell aggregate, they desire a system that controls the cell culture microenvironment around the organoid, increases the quantity of specimens capable of being studied, and improves the ability to perform in situ phenotypic and functional assays without transporting the specimen.

Current platforms for organoid culture include spinning bioreactors, tissue culture plates, and multi-well plates. Spinning bioreactors require a large volume of media to adequately supply nutrients to the organoid or cell aggregate. Bioreactors are also large, which means a large volume of lab space is required for testing. Additionally, if a researcher wishes to change the media, either to add a different nutrient or to administer a drug or other pharmaceutical active ingredient, the researcher must manually change the media by removing the current media from the system. This same manual process of changing the media is present when using tissue culture plates and multi-well plates.

An additional limitation found in current organoid-culture technologies is the inability to perform in situ, image-based end-point analysis on the organoids. Current methods do not provide the transparent or refractive qualities desired for such analysis. What may be required with current systems is manual transportation of the specimen from the culture device, to an imaging-appropriate device, and back. Researchers would benefit from eliminating these extra steps.

What is needed, therefore, is a system that considers the large size of organoids and other large cell aggregates yet also considers the flexibility to provide varying media and the ability to perform analysis within the system. Embodiments of the present disclosure address these concerns as well as other needs that will become apparent upon reading the description below in conjunction with the drawings.

SUMMARY

Briefly described, embodiments of the present disclosure relate generally to mesofluidic devices and methods of using mesofluidic devices, and, more particularly, to mesofluidic devices and methods of using mesofluidic devices for culturing cell aggregates.

According to an aspect of the present invention, a mesofluidic device for culture of cell aggregates is provided. The device may comprise at least one fluid inlet, at least one fluid outlet, a plurality of fluid channels, and a plurality of culture chambers. Each culture chamber may comprise at least one chamber inlet in fluid communication with the at least one fluid inlet via at least one of the plurality of fluid channels, and at least one chamber outlet in fluid communication with the at least one fluid outlet via at least one of the plurality of fluid channels. The mesofluidic device can be configured to contain a cell aggregate in each of the plurality of culture chambers.

In any of the embodiments described herein, the mesofluidic device can further comprise a slide positioned about the mesofluidic device and configured to permit imaging of cell aggregates in the plurality of culture chambers without requiring the cell aggregates to be removed from the culture chambers.

In any of the embodiments described herein, the slide can have an index of refraction between 1.2 and 1.6.

In any of the embodiments described herein, the slide can comprise fluorinated ethylene propylene.

In any of the embodiments described herein, the slide can comprise a cyclic olefin polymer/copolymer.

In any of the embodiments described herein, the slide can comprise glass.

In any of the embodiments described herein, each of the plurality of culture chambers can comprise a first end and a second end, wherein the chamber inlet and the chamber outlet of each culture chamber can be positioned proximate the first end of the corresponding culture chamber.

In any of the embodiments described herein, each of the plurality of culture chambers can comprise a first end and a second end, wherein the chamber inlet of each culture chamber is positioned proximate the first end of the corresponding culture chamber, and wherein the chamber outlet of each culture chamber is positioned proximate the second end of the corresponding culture chamber.

In any of the embodiments described herein, each of the plurality of culture chambers can comprise a biocompatible material.

In any of the embodiments described herein, each of the plurality of culture chambers is dimensioned to hold a cell aggregate having a maximum diameter of from about 100 to 5000 microns.

In any of the embodiments described herein, each of the plurality of culture chambers can be cylindrical.

In any of the embodiments described herein, each of the plurality of cylindrical culture chambers can have a diameter of from about 100 to 7000 microns.

In any of the embodiments described herein, each of the plurality of cylindrical culture chambers can have a height of from about 100 to 5000 microns.

In any of the embodiments described herein, each of the plurality of fluid channels can have a diameter less than a diameter of the cell aggregates.

In any of the embodiments described herein, at least a portion of the plurality of fluid channels have a diameter greater than a diameter of the cell aggregates.

In any of the embodiments described herein, each of the plurality of fluid channels has a diameter less than a diameter of each of the plurality of culture chambers.

In any of the embodiments described herein, each of the plurality of fluid channels can have a diameter of from about 100 to 5000 microns.

In any of the embodiments described herein, each of the plurality of culture chambers can be in fluid communication with one or more other culture chambers in the plurality of culture chambers.

In any of the embodiments described herein, each of the plurality of culture chambers cannot be in fluid communication with any other culture chamber.

In any of the embodiments described herein, the plurality of culture chambers comprises a first culture chamber and a second culture chamber, wherein a chamber inlet of the first culture chamber is in direct fluid communication with a chamber outlet of the second culture chamber via a first fluid channel in the plurality of fluid channels.

In any of the embodiments described herein, each of the plurality of culture chambers can further comprise a cell-aggregate trap configured to receive a cell aggregate from the fluid inlet and deliver the cell aggregate to the corresponding culture chamber via the corresponding chamber inlet.

In any of the embodiments described herein, the cell-aggregate trap of each of the plurality of culture chambers can comprise a trap inlet, a first trap outlet, a second trap outlet, and a cell-aggregate-retention area. The trap inlet can have a diameter greater than a diameter of a cell aggregate to be contained in the corresponding culture chamber. The first trap outlet can have a diameter greater than a diameter of a cell aggregate to be contained in the corresponding culture chamber. The second trap outlet can have a diameter less than a diameter of a cell aggregate to be contained in the corresponding culture chamber. The cell-aggregate-retention area can be in fluid communication with the trap inlet, first trap outlet, and second trap outlet. The cell-aggregate-retention area can be configured to receive a cell aggregate via the trap inlet and pass the cell aggregate to the corresponding culture chamber via the corresponding chamber inlet.

In any of the embodiments described herein, a trap inlet of a first cell-aggregate trap of a first culture chamber in the plurality of culture chambers can be in fluid communication with a first trap outlet of a second cell-aggregate trap of a second culture chamber of the plurality of culture chambers.

In any of the embodiments described herein, a second trap outlet of a first cell-aggregate trap of a first culture chamber in the plurality of culture chambers can be in fluid communication with at least one fluid channel in the plurality of fluid channels.

In any of the embodiments described herein, the second trap outlet of the first cell-aggregate trap of the first culture chamber in the plurality of culture chambers can be in fluid communication with at least one of a trap inlet and a first trap outlet of a second cell-aggregate trap of a second culture chamber in the plurality of culture chambers.

In any of the embodiments described herein, the cell-aggregate trap can be configured to retain a cell aggregate in the cell-aggregate-retention area when the cell-aggregate-retention area comprises a fluid having density greater than or equal to a density of the cell-aggregate.

In any of the embodiments described herein, the cell-aggregate trap can be configured to pass a cell aggregate from the cell-aggregate-retention area to the corresponding culture chamber via the corresponding chamber inlet when the cell-aggregate-retention area comprises a fluid having a density less than a density of the cell-aggregate.

According to another aspect of the present invention, a cell-aggregate trap for loading a cell aggregate in a culture chamber is provided. The cell-aggregate trap can comprise a trap inlet, a first trap outlet, a second trap outlet, and a cell-aggregate-retention area. The trap inlet can have a diameter greater than a diameter of a cell aggregate to be contained in the culture chamber. The trap inlet can be in fluid communication with a fluid inlet. The first trap outlet can have a diameter greater than a diameter of a cell aggregate to be contained in the corresponding culture chamber. The first trap outlet can be in fluid communication with a fluid outlet. The second trap outlet can have a diameter less than a diameter of a cell aggregate to be contained in the corresponding culture chamber. The second trap outlet can be in fluid communication with the fluid outlet. The cell-aggregate-retention area can be in fluid communication with the trap inlet, first trap outlet, and second trap outlet. The cell-aggregate-retention area can be configured to receive a cell aggregate via the trap inlet and pass the cell aggregate to the culture chamber via an aperture in the cell-aggregate-retention area.

In any of the embodiments described herein, the trap inlet can be in fluid communication with a first trap outlet of a second cell-aggregate trap.

In any of the embodiments described herein, the second trap outlet can be in fluid communication with at least one fluid channel.

In any of the embodiments described herein, the second trap outlet can be in fluid communication with a trap inlet and a first trap outlet of a second cell-aggregate trap.

In any of the embodiments described herein, the cell-aggregate trap can be configured to retain a cell aggregate in the cell-aggregate-retention area when the cell-aggregate-retention area comprises a fluid having density greater than or equal to a density of the cell-aggregate.

In any of the embodiments described herein, the cell-aggregate trap can be configured to pass a cell aggregate from the cell-aggregate-retention area to the culture chamber via the aperture when the cell-aggregate-retention area comprises a fluid having a density less than a density of the cell-aggregate.

In any of the embodiments described herein, the trap can comprise a biocompatible material.

In any of the embodiments described herein, the trap inlet and first trap outlet can have diameters of from about 100 to 5000 microns.

According to another aspect of the present invention, a method of culturing cell aggregates in a mesofluidic culture device is provided. The method comprises providing a mesofluidic device comprising at least one fluid inlet, at least one fluid outlet, a plurality of fluid channels, and a plurality of culture chambers, with each culture chamber comprising at least one chamber inlet in fluid communication with the at least one fluid inlet via at least one of the plurality of fluid channels, and at least one channel outlet in fluid communication with the at least one fluid outlet via at least one of the plurality of fluid channels. The mesofluidic device is configured to contain a cell aggregate in each of the plurality of culture chambers. The method can further comprise administering a cell aggregate to each of the plurality of culture chambers, introducing a first fluid to the fluid inlet, and causing at least a portion of the first fluid to flow from the fluid inlet, through the chamber inlet of each of the plurality of culture chambers, through each of the plurality of culture chambers, through the chamber outlet of each of the plurality of culture chambers, and to the fluid outlet.

In any of the embodiments described herein, the fluid can comprise at least one of water, nutrients, phosphate buffered saline, a drug, a pharmaceutical active ingredient, a fluorescent molecule, a dye, and a density gradient medium.

In any of the embodiments described herein, the mesofluidic device further comprises a slide positioned about the mesofluidic device, and method can further comprise imaging cell aggregates in the plurality of culture chambers without removing the cell aggregates from the culture chambers.

In any of the embodiments described herein, causing at least a portion of the first fluid to flow from the fluid inlet, through the chamber inlet of each of the plurality of culture chambers, through each of the plurality of culture chambers, through the chamber outlet of each of the plurality of culture chambers, and to the fluid outlet comprises causing at least a portion of the first fluid to flow from the fluid inlet, through the trap inlet of each cell-aggregate trap of the plurality of culture chambers, through the first fluid outlet of each cell-aggregate trap of the plurality of culture chambers, through the second fluid outlet of each cell-aggregate trap of the plurality of culture chambers, through the chamber inlet of each of the plurality of culture chambers, through each of the plurality of culture chambers, through the chamber outlet of each of the plurality of culture chambers, and to the fluid outlet.

In any of the embodiments described herein, the first fluid can comprise a plurality of cell aggregates, and administering a cell aggregate to each of the plurality of culture chambers comprises causing a cell aggregate in the plurality of cell aggregates to get trapped in the cell-aggregate-retention area of each cell-aggregate trap of the plurality of culture chambers as the first fluid flows through the mesofluidic device.

In any of the embodiments described herein, the first fluid can have a density greater than or equal to a density of each cell aggregate in the plurality of cell aggregates, such that causing at least a portion of the first fluid to flow can cause each of the cell aggregates to be suspended in the cell-aggregate-retention area.

In any of the embodiments described herein, administering a cell aggregate to each of the plurality of culture chambers further comprises introducing a second fluid to the fluid inlet, causing at least a portion of the second fluid to flow from the fluid inlet, through the trap inlet of each cell-aggregate trap of the plurality of culture chambers, through the first fluid outlet of each cell-aggregate trap of the plurality of culture chambers, through the second fluid outlet of each cell-aggregate trap of the plurality of culture chambers, through the chamber inlet of each of the plurality of culture chambers, through each of the plurality of culture chambers, through the chamber outlet of each of the plurality of culture chambers, and to the fluid outlet. The second fluid can have a density less than the density of each cell aggregate in the plurality of cell aggregates, such that causing at least a portion of the second fluid to flow can cause each of the cell aggregates to pass from the cell-aggregate-retention area through the chamber inlet and into the corresponding culture chamber.

In any of the embodiments described herein, administering a cell aggregate to each of the plurality of culture chambers can comprise individually injecting a cell aggregate into each of the plurality of culture chambers.

In any of the embodiments described herein, introducing a first fluid to the fluid inlet can comprise introducing the first fluid to the fluid inlet periodically at defined intervals.

According to another aspect of the present invention, a method of administering a cell aggregate to a culture chamber is provided. The method can comprise providing a mesofluidic device, comprising a fluid inlet, a fluid outlet, a culture chamber, comprising a chamber inlet, and a cell-aggregate trap. The trap can comprise a trap inlet, a first trap outlet, a second trap outlet, and a cell-aggregate-retention area. The trap inlet can have a diameter greater than a diameter of a cell aggregate to be contained in the culture chamber. The trap inlet can be in fluid communication with the fluid inlet. The first trap outlet can have a diameter greater than a diameter of the cell aggregate to be contained in the corresponding culture chamber. The first trap outlet can be in fluid communication with the fluid outlet. The second trap outlet can have a diameter less than a diameter of a cell aggregate to be contained in the corresponding culture chamber. The second trap outlet can be in fluid communication with the fluid outlet. The cell-aggregate-retention area can be in fluid communication with the trap inlet, first trap outlet, and second trap outlet. The method can further comprise introducing a first fluid to the fluid inlet, in which the first fluid comprises a plurality of cell aggregates and the first fluid has a density greater than or equal to a density of the plurality of cell aggregates. The method can further comprise causing at least a portion of the first fluid to flow from the fluid inlet, through the trap inlet, through the cell-aggregate-retention area, through the second trap outlet, through the chamber inlet, through the culture chamber, and to the fluid outlet, such that a cell aggregate in the plurality of cell aggregates becomes suspended in the cell-aggregate-retention area.

In any of the embodiments described herein, the method can further comprise introducing a second fluid to the fluid inlet, in which the second fluid has a density less than a density of the plurality of cell aggregates, and causing at least a portion of the second fluid to flow from the fluid inlet, through the trap inlet, through the cell-aggregate-retention area, through the second trap outlet, through the chamber inlet, through the culture chamber, and to the fluid outlet, such that the cell aggregate suspended in the cell-aggregate-retention area passes through the chamber inlet and into the culture chamber.

In any of the embodiments described herein, the trap inlet can be in fluid communication with a first trap outlet of a second cell-aggregate trap.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE FIGURES

Reference will now be made to the accompanying figures and diagrams, which are not necessarily drawn to scale, and wherein.

DETAILED DESCRIPTION

Figure 1:
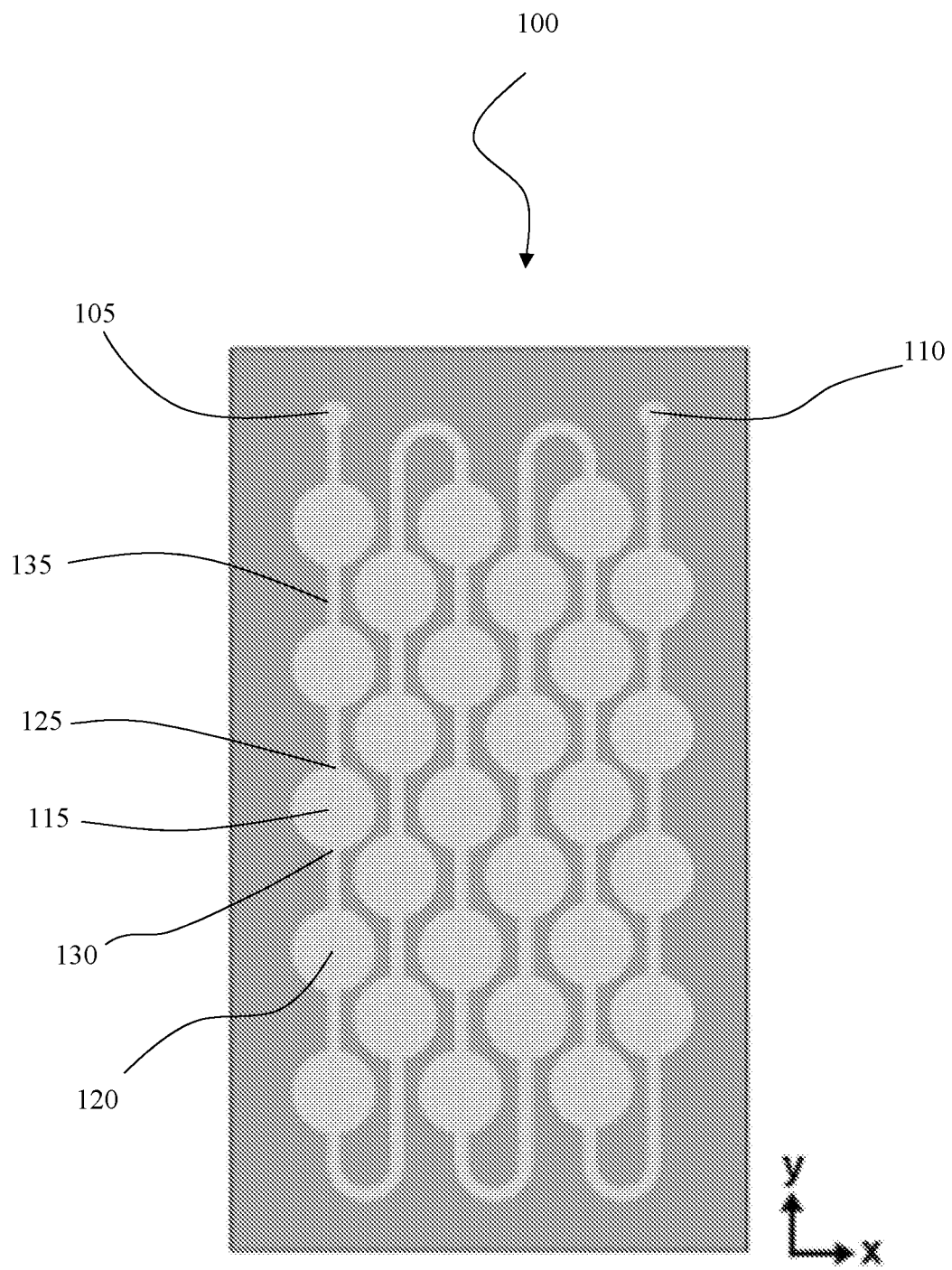
FIG. 1 depicts a top orthogonal view of a mesofluidic device, according to an exemplary embodiment of the present invention.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of being a mesofluidic device for culturing cell aggregates, including organoids. The present disclosure, however, is not so limited and can be applicable in other contexts. For example and not limitation, some embodiments of the present disclosure may improve other fluid delivery systems. Additionally, some embodiments of the present disclosure may improve culture of smaller organisms, such as single cells or smaller biological specimens, or larger organisms, such as large multi-cellular organisms, organs, and the like. These embodiments are contemplated within the scope of the present disclosure. Accordingly, when the present disclosure is described in the context of a mesofluidic device for culturing cell aggregates, it will be understood that other embodiments can take the place of those referred to.

In some embodiments, the present disclosure discusses a mesofluidic device comprising one or more culture chambers for culturing cell aggregates. The device may comprise one or more fluid inlets delivering a fluid into the chamber either directly or by a separate fluid channel(s). The device may comprise one or more fluid outlets wherein the fluid is removed from the one or more culture chambers by the fluid outlet(s) or by a separate fluid channel. It is conceived that, in the case of two or more culture chambers, any culture chamber may be in fluid communication with any other culture chamber. As used herein, two elements are in fluid communication with each other, if during normal operation, fluid from one of the elements would pass to the other element. For example, two culture chambers are in "fluid communication" with each other if at least a portion of the fluid from a fluid inlet enters the first culture chamber, exits the first culture chamber, and enters the second culture chamber (i.e., at least a portion of the fluid flows through both the first and second culture chambers). Two culture chambers are not in fluid communication, however, if no portion of the fluid from the fluid inlet flows in both the first and second culture chambers. Two culture chambers are in "direct fluid communication," e.g., via a fluid channel, if at least a portion of the fluid from a fluid inlet enters the first culture chamber, exits the first culture chamber, and enters the second culture chamber (i.e., at least a portion of the fluid flows through both the first and second culture chambers) without passing through a third culture chamber between the first and second culture chambers. In other embodiments it is conceived that no culture chamber is in fluid communication with any other culture chamber of a plurality of culture chambers. As used herein, a culture chamber is not in fluid communication with another culture chamber if fluid entering the culture chamber did not previously exit another culture chamber and fluid exiting the culture chamber does not subsequently enter another culture chamber.

In some embodiments, the mesofluidic device may comprise a cell-aggregate trap that is configured to capture cell aggregates suspended in a fluid flowing through the device. The cell-aggregate trap may comprise an aperture configured to pass a captured cell aggregate into a culture chamber via a chamber inlet or other aperture. This embodiment provides the user the option to load cell aggregates without manually injecting a cell aggregate into individual culture chambers, e.g., a user is not required to use a pipette to individually inject cell aggregates into culture chambers.

Various devices and methods are disclosed for culturing cell aggregates within a mesofluidic device, and exemplary embodiments of the devices and methods will now be described with reference to the accompanying figures.

FIG. 1 depicts a top orthogonal view of a mesofluidic device 100, according to an exemplary embodiment of the present invention. A mesofluidic device 100 may be manufactured in whole or in part from biocompatible materials. Some features herein will be described as comprising a biocompatible material. Comprising biocompatible materials means that at least the surface of the feature that touches fluid or the cell-aggregate is manufactured from a biocompatible material. A biocompatible material is one that ensures a device does not effectuate a biological response on a specimen. Examples of suitable biocompatible materials include, but are not limited to, polydimethylsiloxane ("PDMS"), poly(methyl methacrylate) ("PMMA"), polystyrene, cyclic olefin (co)polymers ("COCs"), silicones, glass, acrylic, and polysulfone. Certain implementations of the mesofluidic device 100 comprise a single fluid inlet 105 and a single fluid outlet 110. Other implementations of a mesofluidic device 100 comprise multiple fluid inlets and/or multiple fluid outlets.

In some embodiments, a mesofluidic device 100 may comprise a single culture chamber 115. It is conceived that a mesofluidic device 100 may comprise a second culture chamber 120. It is further conceived that a mesofluidic device 100 may comprise a plurality of culture chambers. Some embodiments of a mesofluidic device 100 may comprise 48, 96, 384, or 1536 culture chambers that mimic the positioning of 48-, 96-, 384-, or 1536-well plates. Such an embodiment would allow a mesofluidic device 100 to be used in conjunction with laboratory equipment configured to work with 48-, 96-, 384-, or 1536-well plates, for example multi-channel pipettes. A mesofluidic device 100 disclosed here may have any number of culture chambers 115, depending on the quantity of chambers desired by the user. In some embodiments, a culture chamber 115 may comprise a chamber inlet 125 and a chamber outlet 130.

In some embodiments, a culture chamber 115 may be configured to retain an organoid or other cell aggregate. Organoids are larger than many cellular specimens. To accommodate larger-sized specimens, it is conceived that the diameter of a culture chamber 115 may comprise a range of diameters on the meso-scale. For example and not limitation, culture chambers may have a diameter of from between 100 microns and 7000 microns; culture chambers may have a diameter of from between 100 microns and 6500 microns; culture chambers may have a diameter of from between 100 microns and 6000 microns; culture chambers may have a diameter of from between 100 microns and 5500 microns; culture chambers may have a diameter of from between 100 microns and 5000 microns; culture chambers may have a diameter of from between 100 microns and 4500 microns; culture chambers may have a diameter of from between 100 microns and 4000 microns; culture chambers may have a diameter of from between 100 microns and 3500 microns; culture chambers may have a diameter of from between 100 microns and 3000 microns, culture chambers may have a diameter of from between 100 microns and 2500 microns, or culture chambers may have a diameter of from between 100 microns and 2000 microns. A culture chamber 115 may also have a chamber height in the same ranges as those listed above for the chamber diameter. In other embodiments, a culture chamber 115 may comprise a height of several millimeters, for example about 14 mm, which is the height of a standard 96-well-plate chamber. A culture chamber 115 may comprise any shape desirable for a cellular culture-device. For example and not limitation, the culture chamber may be cylindrical, semi hemispherical, square, polygonal, or any other desired shape.

In some embodiments, a mesofluidic device 100 may comprise one or more fluid channels 135. A fluid channel 135 may be in fluid connection with a chamber inlet 125 and/or a chamber outlet 130 of a culture chamber 115. A fluid channel 135 may be in direct fluid communication with a fluid inlet 105, i.e., fluid from the inlet passes directly to the fluid channel without passing through other elements. For example, in FIG. 1, a second culture chamber 120 is in direct fluid communication with culture chamber 115, i.e., fluid exiting culture chamber 115 flows directly to second culture chamber 120, via a fluid channel. A fluid channel 135 may be in direct fluid communication with a chamber outlet 130 at one end and a chamber inlet 125 at an opposite end, i.e., fluid flows directly from the channel outlet of one culture chamber, through the fluid channel, and to the chamber inlet of another culture chamber. A fluid channel 135 may comprise a diameter configured to allow cell aggregates to flow through the fluid channel 135. For example, a fluid channel 135 may comprise a diameter of from about 100 microns to 5000 microns, or other ranges as contemplated by the diameter of the culture chamber discussed above. In other embodiments, a fluid channel 135 may comprise a diameter configured to prohibit cell aggregates from flowing through the fluid channel 135. In some embodiments, as shown in FIG. 1, a second culture chamber 120 may be in fluid communication with another culture chamber 115. This is because fluid within the device is shared between a culture chamber 115 and second culture chamber 120. For example, in FIG. 1, fluid will leave a culture chamber 115 via a chamber outlet 130 and enter a second culture chamber 120 via a chamber inlet 125. In other embodiments, no two culture chambers are in fluid communication with each other.

Figure 8:
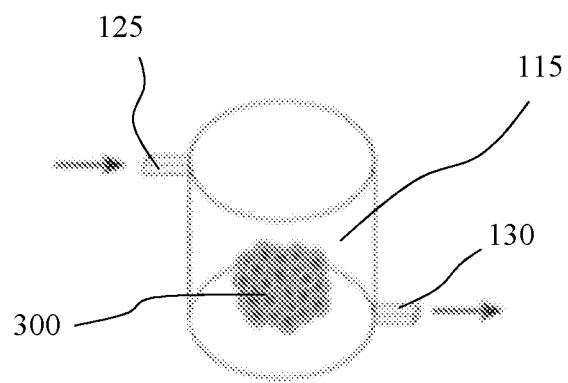
FIG. 8 depicts an orthogonal view of a single culture chamber having an inlet at one end and an outlet at another end, according to an exemplary embodiment of the present invention.

In some embodiments, a culture chamber 115 comprises two ends, a first end and a second end. In FIG. 1, a first end is represented by the top surface of the mesofluidic device 100. A second end would be represented in a z-plane (not pictured in the two-dimensional drawing) set into the mesofluidic device 100, thus creating depth for the culture chamber 115. In some embodiments, a chamber inlet 125 is proximate the first end of the culture chamber 115, and a chamber outlet 130 is proximate the first end of the culture chamber 115. Such a configuration would allow fluid to flow serially from the chamber inlet 125, into the culture chamber 115, and out of the chamber outlet 130. The same serial flow would be found if a chamber inlet 125 and a chamber outlet 130 are both proximate the second end; such a configuration is conceived. In other embodiments, a chamber inlet 125 is proximate a first end of the culture chamber 115, and the chamber outlet 130 is proximate the second end of the culture chamber 115 (an exemplary configuration of such is shown in FIG. 8). Such a configuration would allow fluid to flow diagonally in the z-plane from the chamber inlet 125, through the culture chamber 115, and out of the chamber outlet 130. The same diagonal pattern would be presented if the chamber inlet 125 is proximate the second end and the chamber outlet 130 is proximate the first end; such a configuration is contemplated. This fluid pattern may provide a more uniform fluid flow throughout the culture chamber 115; however, the diagonal flow pattern is not required for a functional mesofluidic device 100. The term "proximate" in this disclosure is defined as "at or substantially close to."

In some embodiments, the fluid flowing through a mesofluidic device 100 may comprise any medium of interest to the user. For example and not limitation, the fluid flowing through a mesofluidic device 100 may comprise any cell culture medium or reagent. A common fluid may comprise phosphate buffered saline (PBS). The fluid may comprise biological matter, such as a biologic or antibodies. The fluid may comprise compounds or materials that a user wishes to introduce to a specimen for analysis, for example a user may introduce drugs or other pharmaceutical active ingredients into the fluid. The fluid may comprise imaging agents, such as florescent molecules or fluorescent dyes. The fluid may contain other reagents for assays such as, but not limited to, immunohistochemistry, fluorescent in situ hybridization, or tissue clearing. The fluid may comprise a solution used to change fluid density, such as Percoll or other density gradient media. An embodiment comprising Percoll or other density gradient media is of particular importance to an embodiment of a mesofluidic device 100 comprising a cell-aggregate trap, which will be discussed in more detail within this disclosure. It is conceived that any other medium, reagent, or additive may be used within a mesofluidic device 100. Fluid may be introduced into a mesofluidic device 100 at one or more fluid inlets 105. The fluid may be introduced via syringe, syringe and corresponding pump, or any other fluid pumping apparatus.

In some embodiments, fluid is introduced into a mesofluidic device 100 through the fluid inlet 105 at rates chosen by the user. For example, a fluid may be introduced into a mesofluidic device 100 continuously over a period of time and at a constant flow rate. During the period of time, the fluid may be changed, yet the flow rate remains constant. In some embodiments, fluid may be introduced at a first flow rate and subsequently changed to a second flow rate. This may be beneficial for a user wishing to analyze the effect of a change in fluid flow rates on a specimen within a culture chamber 115. In other embodiments, the fluid may be perfused though the system at defined intervals. For example, a predetermined volume of fluid may be perfused through a mesofluidic device 100 at a first time-point and again at a second time-point, with no perfusion between the first time-point and the second time-point.

Figure 2:
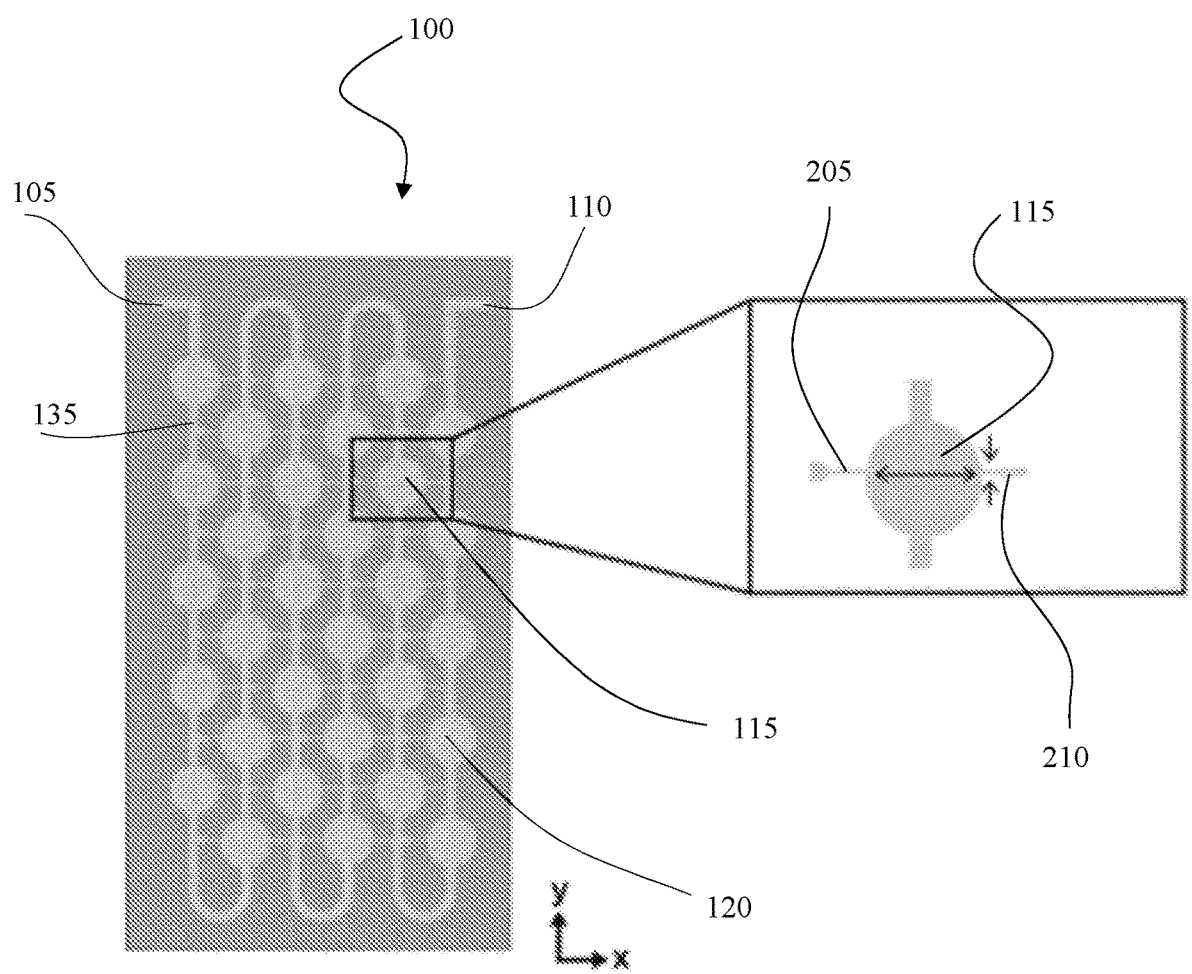
FIG. 2 depicts a top orthogonal view of a mesofluidic device with an exploded detail section, according to an exemplary embodiment of the present invention.

FIG. 2 depicts a top orthogonal view of a mesofluidic device 100 with an exploded detail section of a culture chamber 115, according to an example implementation. In some embodiments, a mesofluidic device may comprise a fluid delivery cross-channel 205 and a fluid removal cross-channel 210. A fluid delivery cross-channel 205 may be in direct fluid communication with a fluid channel 135 at a first end and a culture chamber 115 at a second end. A fluid removal cross-channel 210 may be in direct fluid communication with a culture chamber 115 at a first end and a fluid channel 135 at a second end. The fluid delivery cross-channel 205 and the fluid removal cross-channel 210 can comprise a diameter of from between 100 microns and 5000 microns, or any other ranges discussed above in the context of the diameter of the culture chamber. In an embodiment with a plurality of culture chambers 115, an embodiment with a separate fluid delivery cross-channel 205 and fluid removal cross-channel 210 may provide cross flow from one culture chamber 115 to the next without the fluid flow only flowing in series from one culture chamber 115 to the next via a fluid channel 135. In other words, the cross-channels may improve fluid distribution and fluid sharing because multiple culture chambers 115 are in fluid communication, if such a characteristic is desired. Results from transport modelling analysis showed that a mesofluidic device 100 with a fluid delivery cross-channel 205 and a fluid removal cross-channel 210 provides organoids with significantly similar concentrations of nutrients or metabolites across a plurality of culture chambers.

In some embodiments, not all culture chambers are in direct fluid communication with all other culture chambers in a plurality of culture chambers. For example, in FIG. 2, a second culture chamber 120 is not in direct fluid communication with culture chamber 115. This is because not all fluid exiting culture chamber 115 must necessarily enter second culture chamber 120, although some fluid exiting culture chamber 115 may enter second culture chamber 120.

Figure 3:
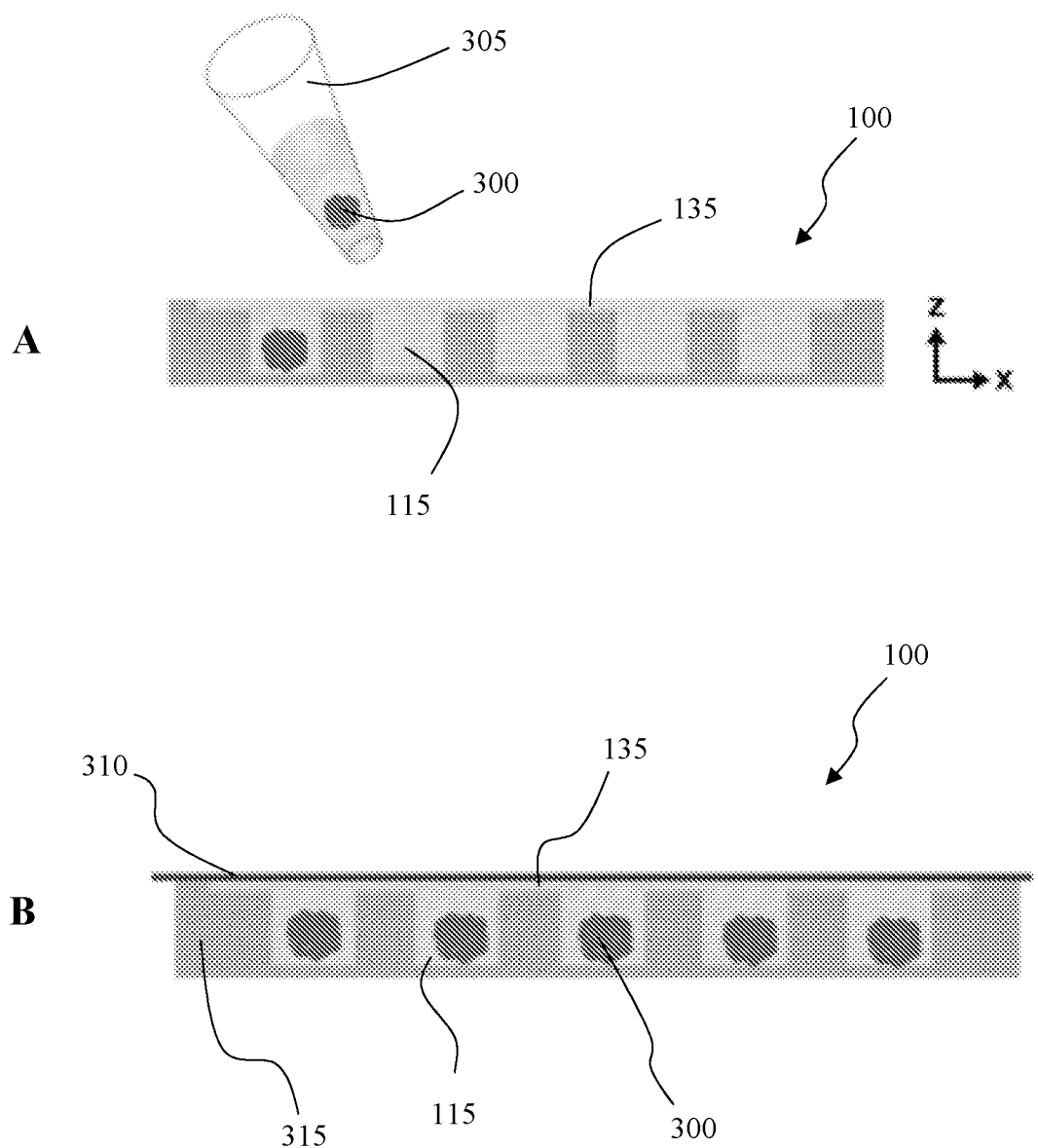
FIG. 3A depicts a process of loading a cell aggregate into a mesofluidic device, according to an exemplary embodiment of the present invention.
FIG. 3B depicts a mesofluidic device with a slide positioned on one surface of the device, according to an exemplary embodiment of the present invention.

FIGS. 3A and 3B depict a side cross-sectional view of a mesofluidic device 100, according to an exemplary embodiment of the present invention. FIG. 3A depicts a process of loading a cell aggregate 300 into a mesofluidic device 100, according to an example implementation. In some embodiments, a cell aggregate 300 may be manually inserted into each culture chamber 115 by individually injecting a cell aggregate 300 using a delivery tool 305. The delivery tool 305 may be a micropipette, pipette, or any other laboratory device configured to deliver a cell aggregate 300. The term cell aggregate includes, but is not limited to, cell aggregates, cell spheroids, tumor spheroids, embryoid bodies, and organoids of any type, such as organoids of the brain, liver, heart, gut, or any other tissue.

FIG. 3B depicts a mesofluidic device 100 with a slide 310 positioned on one surface of the device, according to an example implementation. A slide 310 may comprise any material that may fit onto a surface of the mesofluidic device 100. Any material or combination of materials for slide 310 is conceived. A slide 310 may be positioned about a mesofluidic device 100 to allow visual analysis of the cell aggregate 300 within the culture chamber 115. In some embodiments, a slide 310 comprises a material suitable for imaging-based analysis. Imaging-based analysis techniques include, but are not limited to, bright field analysis, immunohistological analysis, fluorescent imaging, or any other analyses permitted by the passage of light through slide 310. Exemplary materials suitable for imaging-based analysis may include materials that have a low index of refraction as to not distort the image of a specimen within a culture chamber 115. Materials having an index of refraction similar to or less than water (1.33) are conceived as being suitable for imaging-based analysis. Materials conceived as being suitable for imaging-based analysis include: fluorinated ethylene propylene (index of refraction=1.344), glass (1.52), and cyclic olefin copolymer/polymer (1.53). A slide 310 comprising a material having an index of refraction slightly less than water and slightly more than cyclic olefin copolymer/polymer would be considered within a range suitable for imaging-based analysis. Therefore, a slide 310 comprising a material having an index of refraction between 1.2 and 1.6 is contemplated as suitable for imaging-based analysis. In other embodiments, the slide 310 is not suitable for imaging-based analysis because a user is not concerned with imaging the specimen within the culture chamber 115. In such an embodiment, a slide 310 may comprise other materials, including materials having indices of refraction less than 1.2 or greater than 1.6.

In some embodiments, a mesofluidic device 100 may comprise a fluid channel 135 that is open on one side. FIG. 3B depicts an embodiment wherein the top surface of the fluid channel 135 is open and covered by the addition of a slide 310. For example, in the figure, the gap existing between the device body 315 (shown as a shaded area within the mesofluidic device 100) and the slide 310 is the fluid channel 135 formed by adding a slide 310 to the open face of the fluid channel 135. Any other fluid-containing feature could also comprise an open surface that may be closed by a slide 310. For example, a culture chamber 115 and fluid channel 135 may comprise one open surface. It is conceived that the open surface is fluidically sealed by placing a slide 310 about the mesofluidic device 100 to close the one open surface of the culture chamber 115 and fluid channel 135. In some embodiments of this design, a user may apply a slide 310 suitable for image-based analysis to seal the mesofluidic device 100, allowing for visual inspection of all fluid areas within the mesofluidic device 100.

In other embodiments, no slide 310 is required for a mesofluidic device 100 to be sealed. For example, in some embodiments, a culture chamber 115 and fluid channel 135 may be enclosed within the device body 315. In such an embodiment, the only position for fluid entry is at one or more fluid inlets 105 (not shown in FIG. 3B). Other embodiments include a mesofluidic device 100 wherein only a culture chamber 115 comprises an open surface. The open surface can be sealed by positioning a slide 310 on the open surface of the culture chamber 115. In any embodiment comprising a culture chamber 115 having an open surface, a user may administer a cell aggregate into the culture chamber 115 prior to closing the open surface with a slide 310.

In any embodiment, the slide 310 may have any desired dimensions. For example, in some embodiments the slide 310 comprises sufficient surface area to cover at least one culture chamber 115. The slide 310 may also comprise sufficient surface area to cover multiple culture chambers 115, including all culture chambers on the mesofluidic device 100. The slide 310 may also comprise any desired thickness. For example, the slide may be as thin as a laboratory cover slip, having an example thickness of 140 microns. The slide 310 may have a thickness less than a traditional cover slip. Additionally, the thickness of the slide 310 may be greater than the thickness of a traditional cover slip, for example several hundred microns to several millimeters. One limitation for how thin a slide 310 may be is whether the slide may deform if fluid is travelling through any fluid feature below the slide 310. One limitation for how thick a slide 310 may be is having a slide 310 with a sufficient thickness to distort an image of the specimen below the slide 310, if visualization of the specimen is desired.

Figure 4:
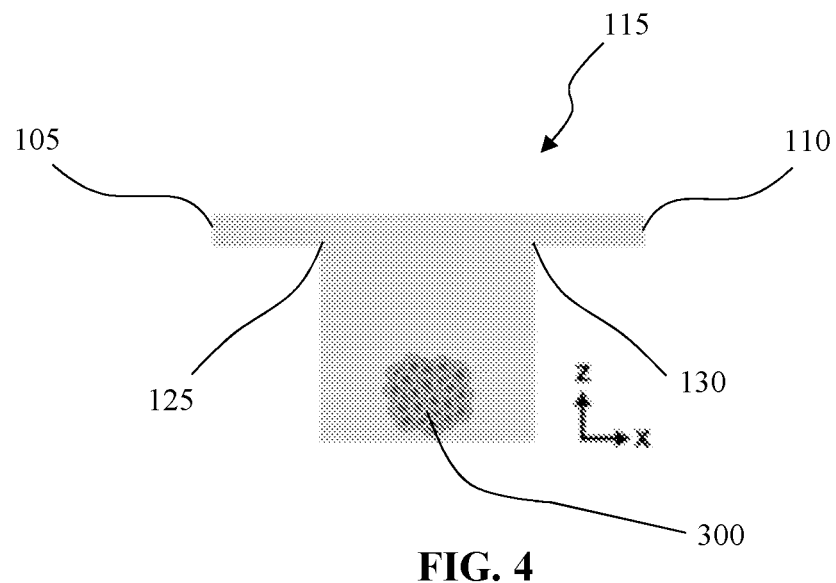
FIG. 4 depicts a side cross-sectional view of a single culture chamber having an inlet and an outlet at the same end, according to an exemplary embodiment of the present invention.

FIG. 4 depicts a side cross-sectional view of a single culture chamber 115, according to an example implementation. In some embodiments, the culture chamber 115 comprises a chamber inlet 125 within the same plane as a chamber outlet 130, as depicted in FIG. 4. An embodiment such as the one shown would cause fluid flowing in through fluid inlet 105 to pass serially from the chamber inlet 125, to the chamber outlet 130, and out through the fluid outlet 110. Other embodiments comprise a chamber inlet 125 in a different plane than chamber outlet 130. For instance, either a chamber inlet 125 or a chamber outlet 130 could be positioned at the bottom of the culture chamber 115, such that fluid flows diagonally through the culture chamber. Other embodiments may comprise either a chamber inlet 125 or a chamber outlet 130 being positioned at a midpoint between the top of culture chamber 115 and the bottom of culture chamber 115. Although FIG. 4 depicts a culture chamber 115 comprising a single inlet and a single, the disclosure considerers embodiments with a plurality of inlets and/or outlets.

Figure 5:
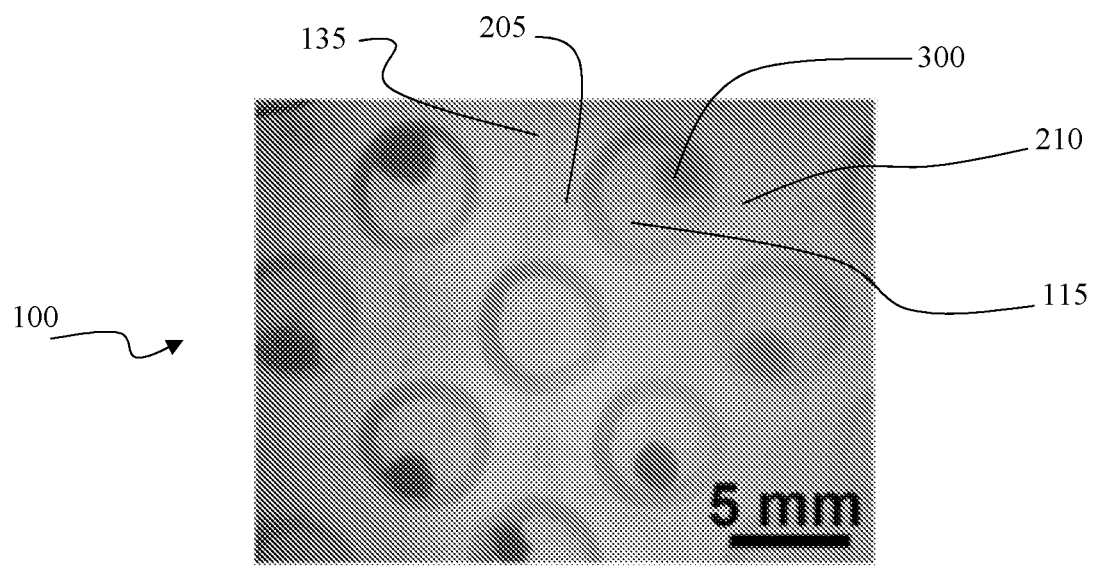
FIG. 5 depicts a bright field image of culture chambers containing cell aggregates, according to an exemplary embodiment of the present invention.

FIG. 5 depicts a bright field image of culture chambers 115 containing cell aggregates 300, according to an example implementation. The cell aggregates 300 in the figure are forebrain organoids. The bright field image captures use of an embodiment as depicted in FIG. 2, wherein the mesofluidic device 100 comprises a fluid delivery cross-channel 205 and a fluid removal cross-channel 210. In the embodiment depicted, each of the plurality of culture chambers 115 comprise a dimeter of 5 mm. The 5 mm diameter is sufficient to contain large organoids or other cell aggregates. Cell aggregates 300 having a diameter of approximately 2 mm are shown in seven culture chambers 115 of the mesofluidic device 100 depicted.

The embodiment shown in FIG. 5 also comprises visible fluid channels 135, fluid delivery cross-channels 205, and fluid removal cross-channels 210. The fluid channels 135 of the device depicted in FIG. 5 comprised a dimeter of 700 microns. Other embodiments may comprise smaller or larger fluid channels. For example, some embodiments may comprise fluid channels 135 having a diameter greater than the diameter of the cell aggregate 300, such that an organoid may flow through the fluid channels 135. The fluid delivery cross-channels 205 and fluid removal cross-channels 210 each have diameters of 200 microns in the embodiment depicted in FIG. 5. Again, these channels may have diameters less than or greater than 200 microns. Any of the fluid channels 135, fluid delivery cross-channels 205, or fluid removal cross-channels 210 may have diameters between 100 microns and 5000 microns.

Also shown in FIG. 5 is a mesofluidic device 100 wherein the top surface of the device is covered with a slide 310. The slide 310 is not shown in the figure because the slide 310 comprises a transparent material. The fluid channels 135, fluid delivery cross-channels 205, fluid removal cross-channels 210, and culture chambers 115 all comprise an open top surface in the embodiment depicted. The transparency of the slide, along with its low index of refraction (glass: 1.52), provided easy analysis of the cultures within the device. In the embodiment shown, bright field analysis, immunohistological analysis, or any other analyses may be performed directly on the cultured cell aggregates 300.

Figure 6:
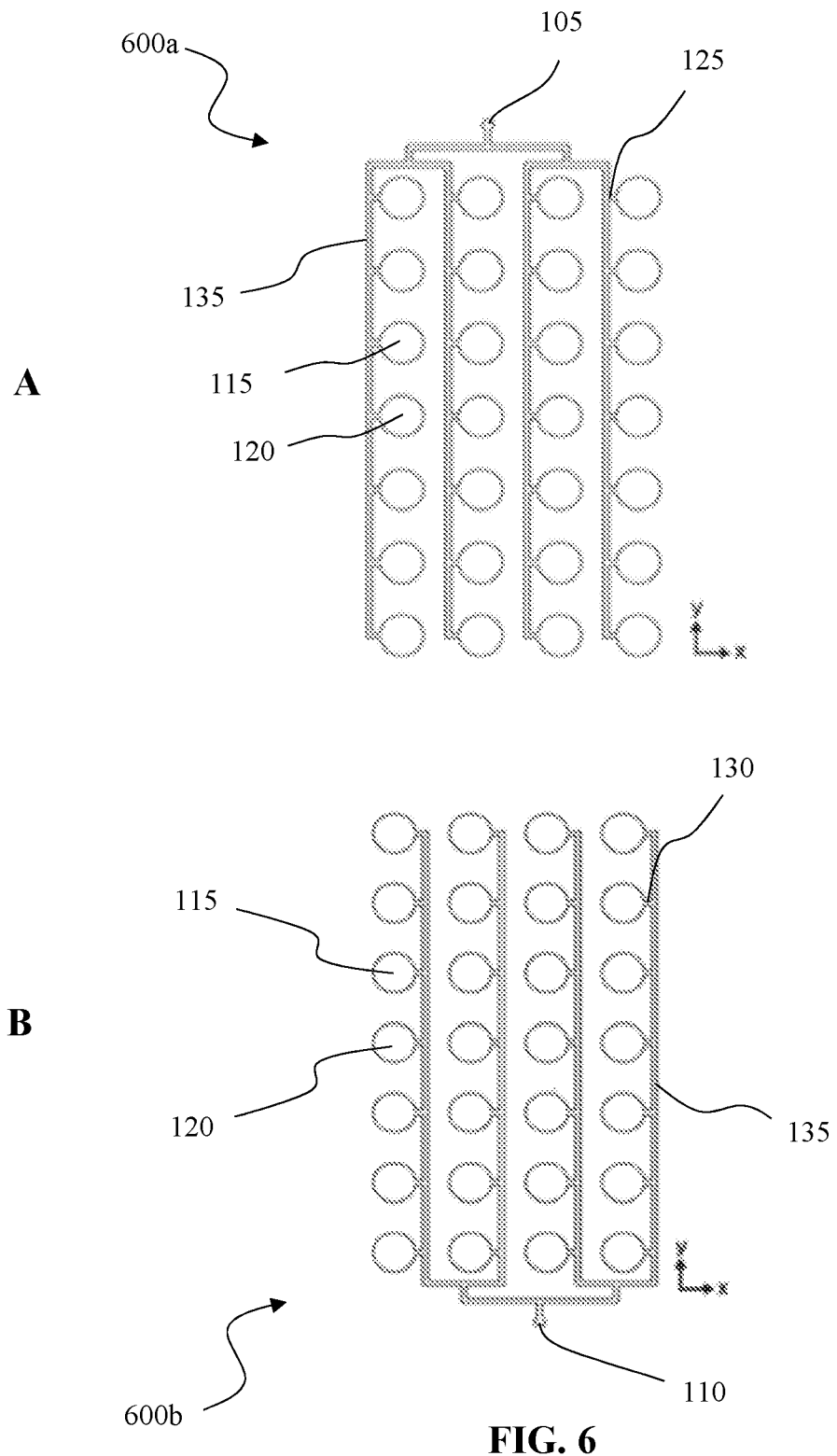
FIG. 6A depicts an embodiment of a mesofluidic device comprising a separate first body, according to an exemplary embodiment of the present invention.
FIG. 6B depicts an embodiment of a mesofluidic device comprising a separate second body, according to an exemplary embodiment of the present invention.

FIGS. 6A and 6B depict top orthogonal views of a mesofluidic device 100, according to an example implementation. Some embodiments of a mesofluidic device 100 comprise two separate bodies, a first body 600a and a second body 600b. FIG. 6A depicts an embodiment of a mesofluidic device 100 comprising a first body 600a, according to an example implementation. In some embodiments, the first body 600a comprises a fluid inlet 105, wherein a fluid inlet 105 provides fluid to one or more fluid channels 135. A fluid channel 135 may connect to one or more culture chambers 115. As shown in FIG. 6A, a single fluid channel 135 may supply fluid to a plurality of chamber inlets 125. In an embodiment wherein one fluid channel 135 supplies fluid to a plurality of chamber inlets 125, a second culture chamber 120 is not in fluid communication with a first culture chamber 115. This is because no fluid necessarily passes from one culture chamber to another culture chamber.

FIG. 6B depicts an embodiment of a mesofluidic device 100 comprising a second body 600b, according to an example implementation. In some embodiments, the second body 600b comprises a fluid outlet 110, wherein a fluid outlet 110 removes fluid from one or more fluid channels 135. A fluid channel 135 may connect to one or more culture chambers 115. As shown in FIG. 6B, a single fluid channel 135 may remove fluid from a plurality of chamber outlets 130. In an embodiment wherein one fluid channel 135 removes fluid from a plurality of chamber outlets 130, a second culture chamber 120 is not in fluid communication with a first culture chamber 115. This is because no fluid necessarily passes from one culture chamber to another culture chamber.

Figure 7:
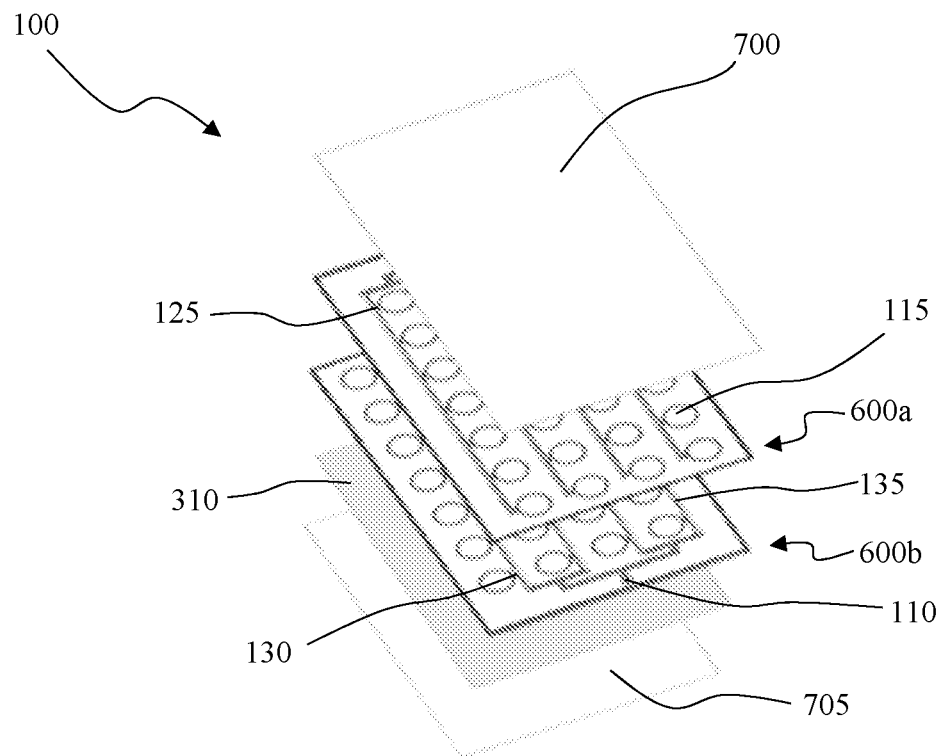
FIG. 7 depicts an orthogonal exploded view of a mesofluidic device comprising multiple bodies, according to an exemplary embodiment of the present invention.

FIG. 7 depicts an orthogonal exploded view of a mesofluidic device 100, according to an example implementation. In some embodiments, the mesofluidic device 100 comprises a first body 600a and a second body 600b. In some embodiments, the first body 600a is stacked above or below the second body 600b. The culture chambers 115 of the first body 600a and the second body 600b may combine to form a single culture chamber. Because it is conceived that height of a culture chamber 115 may be, for example, from between 100 microns and 7000 microns, a portion of the height of a culture chamber 115 may be found in the thickness of the first body 600a and a portion of the height of a culture chamber 115 may be found in the thickness of the second body 600b.

In some embodiments, a first clamp surface 700 may be placed about a surface of the device. In some embodiments, a second clamp surface 705 may be placed about a different surface of the device. The first clamp surface 700 and the second clamp surface 705 may comprise any material. The first clamp surface 700 and the second clamp surface 705 assist in adding a compressive force to the mesofluidic device 100 such that a first body 600a and a second body 600b remain compressed together. In some embodiments, either a first clamp surface 700 or a second clamp surface 705, or both, may comprise a material suitable for imaging-based analysis. This would allow the clamps to maintain compressive force yet also allow a user to analyze the fluid or specimens within the device. In other embodiments, a first clamp surface 700 or a second clamp surface 705 does not comprise a material suitable for imaging-based analysis. In these embodiments, the purpose of a first clamp surface 700 or a second clamp surface 705 can be for compressing a first body 600a and a second body 600b together.

In some embodiments, a slide 310 is positioned about a surface of the mesofluidic device 100. If either a first clamp surface 700 or a second clamp surface 705 is not suitable for imaging-based analysis, a slide 310 that is suitable may be positioned about any surface to allow analysis of the fluid or specimens within the device.

In some embodiments with a plurality of culture chambers 115, no two culture chambers 115 are in fluid communication with any other culture chambers. For example, in FIG. 7, all chamber inlets 125 are positioned in a first body 600a, while all chamber outlets 130 are positioned in a second body 600b. Fluid that enters any culture chamber 115 will exit a chamber outlet 130 on the second body 600b, will flow to a fluid channel 135 on the second body 600b, and will exit the mesofluidic device 100 at a fluid outlet 110. This design prevents any fluid within the device from being shared between any two culture chambers 115.

Although some embodiments conceive a first body 600a separate from a second body 600b, it is not necessary that both features be separate. For example, a mesofluidic device 100 may comprise a single body having a first side and a second side. A first side could comprise a fluid inlet, fluid channels, and chamber inlets. A second side could comprise a fluid outlet, a separate set of fluid channels, and chamber outlets. A chamber inlet of the first side of the device could be in fluid connection with a corresponding chamber outlet of the second side of the device. This embodiment would create the same effect as the device shown in FIG. 7, yet there would be only one device body.

FIG. 8 depicts an orthogonal view of a single culture chamber 115, according to an exemplary embodiment of the present invention. In some embodiments, as shown in FIG. 8, a culture chamber 115 comprises a chamber inlet 125 at a first end and a chamber outlet 130 at a second end. Such an embodiment creates a cross flow at an angle across the culture chamber 115, creating convective flow around a cell aggregate 300.

Figure 9:
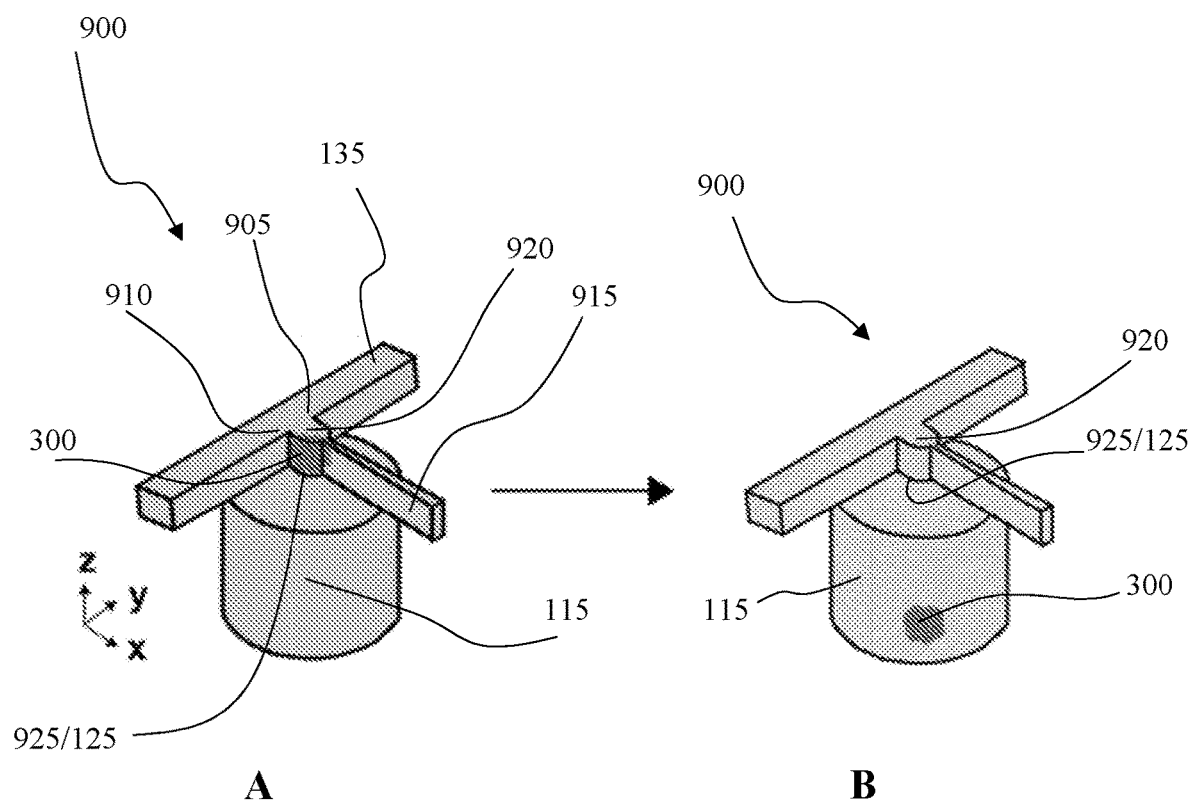
FIG. 9A depicts an orthogonal view of a cell-aggregate trap with a captured cell aggregate, according to an exemplary embodiment of the present invention.
FIG. 9B depicts an orthogonal view of a cell-aggregate trap with a cell aggregate loaded into a culture chamber, according to an exemplary embodiment of the present invention.

FIGS. 9A and 9B depict an orthogonal view of a cell-aggregate trap 900, according to an exemplary embodiment of the present invention. FIG. 9A depicts an orthogonal view of a cell-aggregate trap 900 with a captured cell aggregate 300, according to an example implementation. In some embodiments, any device described herein may comprise a cell-aggregate trap 900. A cell-aggregate trap 900 may comprise a trap inlet 905. A cell-aggregate trap 900 may comprise a first trap outlet 910. A cell-aggregate trap may comprise a second trap outlet 915. A cell-aggregate trap 900 may comprise a cell-aggregate-retention area 920. The cell-aggregate trap 900 is configured to retain cell aggregates 300 that are suspended in a fluid that passes through the cell-aggregate trap 900. In some embodiments, a fluid will flow into the cell-aggregate trap 900 from a fluid channel 135. The fluid may comprise a quantity of cell aggregates 300 suspended within the fluid. When a cell aggregate 300 approaches a trap inlet 905, the cell aggregate will enter the cell-aggregate-retention area 920. The cell aggregate 300 will then remain suspended within the cell-aggregate-retention area 920. Any subsequent cell aggregates 300 that flow through the cell-aggregate trap 900 will pass the occupied cell-aggregate-retention area 920, will exit through the first trap outlet 910, and will continue through the fluid channel 135.

A cell-aggregate trap 900 may comprise an aperture 925 along one surface of the cell-aggregate-retention area 920. In some embodiments, an aperture 925 may be a hole between the cell-aggregate-retention area 920 and culture chamber 115 that opens directly into a chamber inlet 125 of a culture chamber 115. In some embodiments, an aperture 925 may comprise a longer channel leading to a chamber inlet 125. In some embodiments, the aperture 925 may serve as the chamber inlet 125, as shown in the exemplary embodiments depicted FIGS. 9A and 9B by reference to one integrated feature.

In embodiments with a cell-aggregate trap 900, it is essential that a fluid channel 135, a trap inlet 905, and a first trap outlet 910 comprise a diameter that is greater than a diameter of a cell aggregate 300. This diameter may be between 100 microns and 5000 microns, depending on the size of the cell aggregate 300 being studied in the device. A second trap outlet 915 can comprise a diameter less than the diameter of a cell aggregate 300. A second trap outlet 915 with a diameter smaller than a cell aggregate 300 creates two benefits for a cell-aggregate trap 900. First, a when a cell aggregate 300 is larger than the second trap outlet 915, the cell aggregate 300 cannot pass through the outlet. This allows the cell aggregate 300 to remain in the cell-aggregate-retention area 920, blocking subsequent cell aggregates from entering the area. Second, a second trap outlet 915 with a diameter smaller than the trap inlet 905 and fluid channel 135, when blocked by an already loaded cell aggregate, redirects flow that carries additional aggregates along the fluid channel 135 to the subsequent traps.

FIG. 9A further depicts a culture chamber 115 positioned about the cell-aggregate trap 900. In some embodiments, a user may take advantage of the cell-aggregate trap 900 by creating a hydrodynamic loading mechanism for loading a cell aggregate 300 into a culture chamber 115. In some embodiments of the present disclosure, a first fluid comprising a cell aggregate 300 is introduced into a device comprising a cell-aggregate trap 900, wherein the first fluid has a fluid density equal to or greater than the density of the cell aggregate 300. The first fluid may be introduced into the device, wherein the first fluid will flow from a fluid channel 135, into the trap inlet 905, into the culture chamber 115, out of the second trap outlet 915, and out of the first trap outlet 910. When a cell aggregate 300 suspended in the first fluid enters the trap inlet 905, the cell aggregate 300 will enter the cell-aggregate-retention area 920 and remain suspended within the cell-aggregate-retention area 920. Thereafter, a second fluid having a density less than the density of the cell aggregate 300 may be introduced into the device. When the second fluid replaces a portion of the first fluid, the cell aggregate 300 will exit the cell-aggregate-retention area 920 and enter the culture chamber 115 via the aperture 925 and chamber inlet 125. The greater density of the cell aggregate 300 will overcome gravity in the cell-aggregate-retention area 920, and the cell aggregate 300 will enter a culture chamber 115 positioned below the cell-aggregate-retention area 920.

In some embodiments, the second trap outlet 915 may be tapered such that the diameter of the outlet is smaller at one end than the other end. For example, a second trap outlet 915 may have a first diameter at the location where the second trap outlet 915 meets the cell-aggregate-retention area 920. The first diameter may be smaller than the diameter of the cell aggregate 300 to prohibit the cell aggregate 300 from passing through the second trap outlet 915. The second trap outlet 915 may then taper such that it has a second diameter at a position distant from the location where the second trap outlet 915 meets the cell-aggregate-retention area 920, the second diameter being larger than the first diameter. This embodiment may decrease fluidic resistance and allow more fluid to exit the cell-aggregate-retention area 920 than in an embodiment having a second trap outlet 915 with one dimeter across the length of the outlet.

FIG. 9B depicts an orthogonal view of a cell-aggregate trap 900 with a cell aggregate 300 loaded into a culture chamber 115, according to an example implementation. As described within this disclosure, in some embodiments a cell aggregate 300 may be introduced into a culture chamber 115 via a hydrodynamic loading mechanism. The hydrodynamic loading mechanism comprises the process of (i) suspending a cell aggregate 300 in a first fluid, the first fluid having a density greater than or equal to the density of the cell aggregate 300, (ii) introducing the first fluid into the cell-aggregate trap 900, (iii) allowing the suspended cell aggregate 300 to be captured in a cell-aggregate-retention area 920, and (iv) introducing a second fluid having a density less than the cell aggregate 300, thereby causing the captured cell aggregate 300 to pass into a culture chamber 115. One contemplated method of reducing the density of a fluid within the device is to introduce a density gradient medium, such a Percoll, into the first fluid. Other methods may comprise introducing a second fluid that inherently has a lesser density than a cell aggregate 300. FIG. 9B depicts an example embodiment after a fluid with a density less than a cell aggregate 300 has been introduced to the device, thereby allowing the cell aggregate 300 to enter the culture chamber 115.

In some embodiments, the culture chamber 115 of the cell-aggregate trap 900 may comprise a chamber inlet 125 positioned between the cell-aggregate-retention area 920 and the culture chamber 115. A chamber inlet 125 may be a hole between the cell-aggregate-retention area 920 and culture chamber 115 that opens directly into the culture chamber 115. In some embodiments, a chamber inlet 125 may comprise a longer channel leading to an aperture 925. In some embodiments, the aperture 925 may serve as the chamber inlet 125, as shown in the exemplary embodiments depicted in FIGS. 9A and 9B by reference to one integrated feature. In some embodiments, the cell-aggregate trap 900 may comprise a chamber outlet (not shown in FIG. 9) positioned within the culture chamber 115 at a distance from aperture 925 and/or chamber inlet 125. In such an embodiment, fluid may exit the culture chamber 115 from either the second trap outlet 915, the first trap outlet 910, or the chamber outlet.

Figure 10:
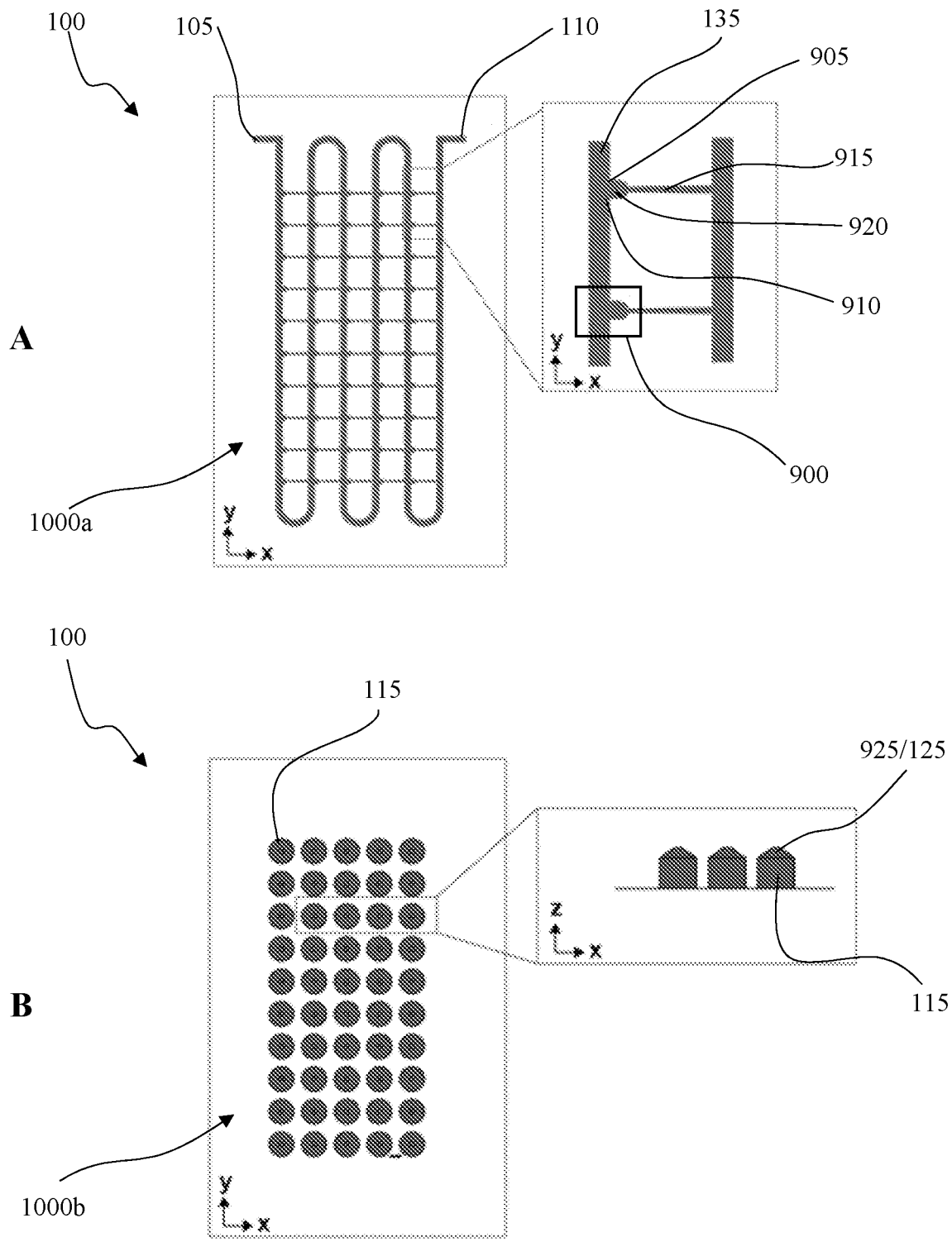
FIG. 10A depicts a top orthogonal view of a first trap-plate of a multi-plate cell-aggregate trap device, according to an exemplary embodiment of the present invention.
FIG. 10B depicts a top orthogonal view of a second trap-plate of a multi-plate cell-aggregate trap device, according to an exemplary embodiment of the present invention.

FIGS. 10A and 10B depict top orthogonal views of a mesofluidic device 100, wherein the mesofluidic device 100 comprises a first trap-plate 1000a and a second trap-plate 1000b, according to an example implementation. In some embodiments, a mesofluidic device 100 may comprise separate surfaces, including a first trap-plate 1000a and a second trap-plate 1000b. FIG. 10A depicts a top orthogonal view of a first trap-plate 1000a, according to an example implementation. In some embodiments, the first trap-plate 1000a comprises a fluid inlet 105, a fluid channel 135, a trap inlet 905, a cell-aggregate-retention area 920, a first trap outlet 910, a second trap outlet 915, and a fluid outlet 110. In some embodiments, the first trap-plate 1000a comprises a plurality of cell-aggregate traps 900. In an embodiment where a user perfuses a fluid containing a plurality of cell aggregates, it may be desired to use a mesofluidic device 100 having a plurality of cell-aggregate traps 900. For example, FIG. 10A depicts a first trap-plate 1000a comprising fifty (50) cell-aggregate traps 900. If a user introduces a fluid comprising up to 50 cell aggregates, the first trap-plate 1000a may capture every cell aggregate. It may be beneficial to introduce a greater quantity of cell aggregates than the first trap-plate 1000a comprises cell-aggregate-retention areas 920, thereby creating a better probability that all cell-aggregate-retention areas 920 capture a cell aggregate. It other situations, it may be beneficial to introduce a smaller quantity of cell aggregates than the first trap-plate 1000a comprises cell-aggregate-retention areas 920, thereby ensuring or increasing the likelihood that all cell aggregates within the fluid become trapped within a cell-aggregate-retention area 920.

It is conceived that the first trap-plate 1000a may comprise any quantity of cell-aggregate traps 900. For example, in some embodiments, the first trap-plate 1000a may comprise a quantity of cell-aggregate traps 900 equal to a quantity of culture chambers 115 within a second trap-plate 1000b. In some embodiments, the first trap-plate 1000a may comprise 48, 96, 384, or 1536 cell-aggregate traps 900, each trap being spaced as to be positioned above a microwell in a corresponding standard 48-, 96-, 384-, or 1536-well plate.

In some embodiments, the first trap-plate 1000a comprises an aperture 925 located on one side of the cell-aggregate-retention area 920, the aperture 925 opening to a chamber inlet 125. This feature is not depicted in this two-dimensional drawing, but the location of the aperture 925 is represented in FIG. 10B as one integrated feature with a chamber inlet 125.

FIG. 10B depicts a top orthogonal view of a second trap-plate 1000b, according to an example embodiment. In some embodiments, a second trap-plate 1000b comprises a single culture chamber 115. In other embodiments, the second trap-plate 1000b comprises a plurality of culture chambers 115. In some embodiments, a culture chamber may comprise a chamber inlet 125. The chamber inlet 125 may be in fluid connection with an aperture 925 located on one surface of the cell-aggregate-retention area 920. In some embodiments, as depicted in FIG. 10B, a chamber inlet 125 and an aperture 925 may be integrated into one feature.

It is beneficial for a second trap-plate 1000b to comprise a culture chamber 115 at a position below a cell-aggregate-retention area 920 and aperture 925 of a corresponding first trap-plate 1000a. This allows a culture chamber 115 of the second trap-plate 1000b to capture a cell aggregate exiting a cell-aggregate-retention area 920, exiting an aperture 925, and entering a chamber inlet 125 of a corresponding culture chamber 115.

It is conceived that a second trap-plate 1000b may comprise any quantity of culture chambers 1000b. In some embodiments, a second trap-plate 1000b may be custom fabricated with a quantity of culture chambers 115 to be used with a first trap-plate 1000a. In other embodiments, the second trap-plate 1000b may be a standard 48-, 96-, 384-, or 1536-well plate, wherein a first trap-plate 1000a is positioned above the standard 48-, 96-, 384-, or 1536-well plate. A culture chamber 115 may be sized such that the culture chamber 115 is appropriate for cell aggregates of different sizes, as described in the present disclosure.

It is conceived that a standard 48-, 96-, 384-, or 1536-well plate may be used with a cell-aggregate-trap system described herein. A 48-well plate comprises 48 culture chambers, each having a diameter of about 9800 microns. Although the diameter of each culture chamber in a 48-well plate may be large compared to some cell aggregates, it is conceived that such a diameter may be beneficial, and therefore such a diameter is conceived in this disclosure.

In some embodiments, it is conceived that a mesofluidic device 100 comprises one integrated plate. For example, in lieu of a mesofluidic device 100 comprising a first trap-plate 1000a and a second trap-plate 1000b, the mesofluidic device 100 may comprise a single body having a combined first trap-plate 1000a and second trap-plate 1000b.

Figure 11:
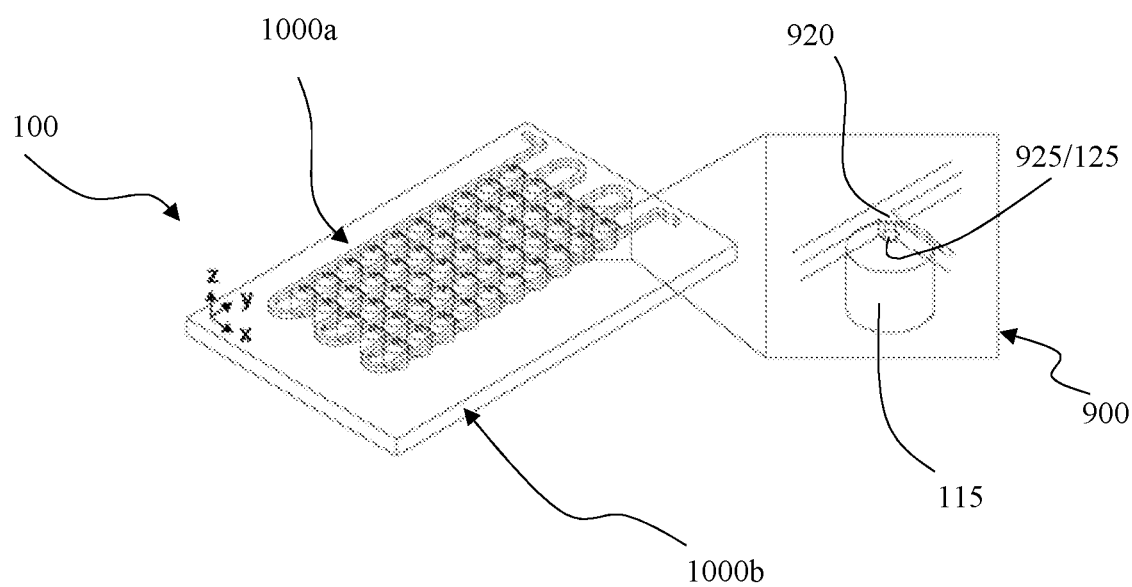
FIG. 11 depicts an orthogonal view of a mesofluidic device with a first trap-plate positioned above a second trap-plate, according to an exemplary embodiment of the present invention.

FIG. 11 depicts an orthogonal view of a mesofluidic device 100 with a first trap-plate 1000a positioned above a second trap-plate 1000b, according to an example implementation. In some embodiments, a first trap-plate 1000a may be positioned above a second trap-plate 1000b such that a cell aggregate may be delivered to a culture chamber 115 via the hydrodynamic loading mechanism described herein. In some embodiments, a first trap-plate 1000a may comprise a material and a thickness that is suitable for imaging-based analysis. In such an embodiment, it is possible to analyze cell aggregates trapped within the cell-aggregate-retention area 920. It is also possible to analyze cell aggregates held within a culture chamber 115 after the cell aggregate has passed from a cell-aggregate-retention area 920, through an aperture 925, and into a culture chamber 115. The analysis can be performed directly though the first trap-plate 1000a. The analysis may also be performed directly through the bottom of the second trap-plate 1000b. A slide (not pictured in FIG. 11) may also be positioned below the second trap-plate 1000b.

In some embodiments, the first trap-plate 1000a may be removed from the mesofluidic device 100 prior to imaging-based analysis. In such an embodiment, a user may place a slide (not pictured in FIG. 11) about the device in the place of the removed first trap-plate 1000a. In some embodiments, the slide may comprise a material and a thickness that is suitable for imaging-based analysis, as described herein.

Design Considerations

The present disclosure improves upon previous devices by improving fluid delivery to larger specimens, such as organoids and other large cell aggregates. The mesofluidic device described here can solve many of the problems associated with culturing specimens on the meso scale, or rather specimens that fall somewhere between the micro scale (a few microns in diameter) and macro scale (several millimeters in diameter).

Microfluidic devices, which have features on the micrometer scale, can be made using conventional photolithography and soft lithography techniques. These processes can yield channel and other feature sizes ranging from ~10 μm to ~500 μm. It is difficult to fabricate features larger than 500 μm with these methods. Organoids on the order of 2 to 5 millimeters can therefore not be used within such devices.

In contrast to devices with micro-scale features, devices with macro-scale feature sizes of several millimeters and larger can be fabricated using a variety of techniques such as micromilling and micromachining. These techniques generally cannot fabricate features less than a millimeter with good resolution. In many of the embodiments described herein, channels and other features were in the range of a few hundred microns. Therefore, macro-scale devices are not optimal for providing consistent and controllable media to organoids.

More recently, stereolithography and 3D printing have been used to create feature sizes as small as a few hundred microns and as large as tens of millimeters. However, the specific stereolithography and 3D printing methods, equipment, and materials vary widely in terms of the minimum features sizes, resolution, maximum overall device size, and surface roughness of the final part. Thus, it is non-trivial to evaluate, adapt, and optimize these manufacturing methods for fabrication of mesofluidic devices or molds for mesofluidic devices.

Several design considerations are presented when designing meso-sized devices for the culture of cell aggregates. First, the culture chambers holding the cell aggregates must be large enough to support the maximum size of larger cell aggregates, such as organoids. Second, the channels, inlets, and outlets used to deliver fluid to the cell aggregates must be small enough or oriented in such a way that the cell aggregates are retained within the culture chambers when fluids are introduced into the chambers. For example, if the channels, inlets, or outlets are too large, cell aggregates that begin small can be unintentionally expelled from the chambers. Third, the orientation of the fluid channels, inlets, and outlets must be designed so that there is good control over fluid exchange in the chambers. In this respect, it is more difficult to design fluid channels to deliver fluids to the chambers compared to micro-scale devices. For devices on the meso-scale, mass transport by diffusion is slower than compared to their micro-scale counterparts (as the time scale of mass diffusion across a device scales with distance across the device squared). Without sufficient mass transport to the chambers, insufficient growth medium, waste, and reagents will be transported to and from the cell aggregates. Thus, it is critical to carefully design mesofluidic devices to ensure that there is convective mass transport through the chambers.

Figure 12:
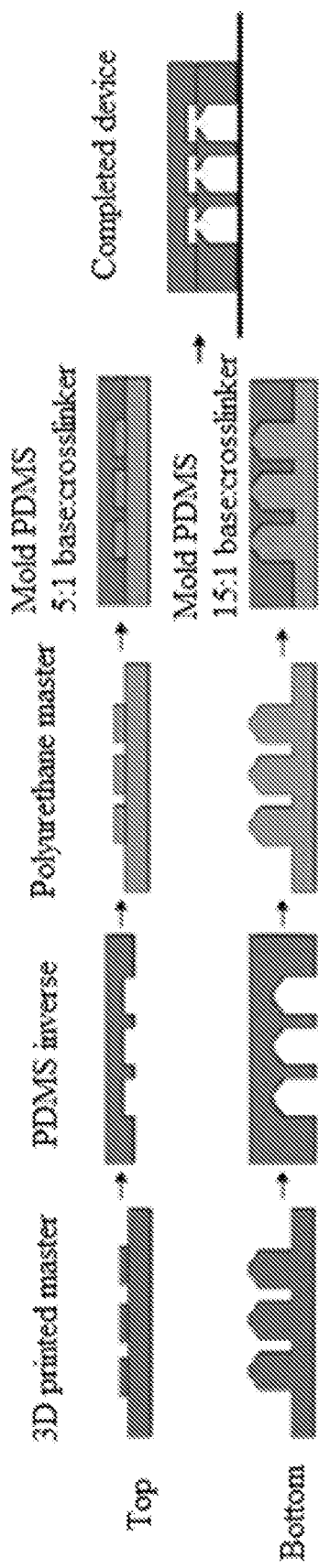
FIG. 12 depicts one fabrication method for creating a mesofluidic device, according to an exemplary embodiment of the present invention.

These design considerations were all contemplated when creating various embodiments of the devices described in this disclosure. An exemplary fabrication method for creating a mesofluidic device is presented in FIG. 12. Device designs were drawn in SolidWorks. Master molds for the devices were made by 3D printing the molds. For devices with smaller features, such as the 200-micron cross-channels shown in the exemplary embodiment depicted in FIG. 5, master molds were 3D printed by the company Protolabs in the material MicroFine Green. For devices with larger footprints, such as devices having channels with diameters in the range of 600 microns, master molds were printed in Accura SL 5530.

Inverses of the master molds were made from PDMS using soft lithography. Additional master molds may be fabricated with more durable materials, such as polyurethane, by using the PDMS inverses. In exemplary iterations of various devices described herein, mesofluidic devices were made by pouring PDMS onto master molds. In various iterations, the PDMS was mixed in either a 5:1, 10:1, or 15:1 ratio of pre-polymer base to crosslinker. Any other ratio of base to crosslinker is conceived; the ratio may be adjusted to achieve a desired characteristic, such as stiffness. Furthermore, the utility of the mesofluidic devices are not limited to use of PDMS.

Experimental Section

The following section presents results from testing three exemplary embodiments of devices described in this disclosure. Experimentation was conducted to determine any improvement over current culture methods. The following embodiments are not inclusive of all device designs described within this disclosure.

Methods of Design Iteration 1

Figure 13:
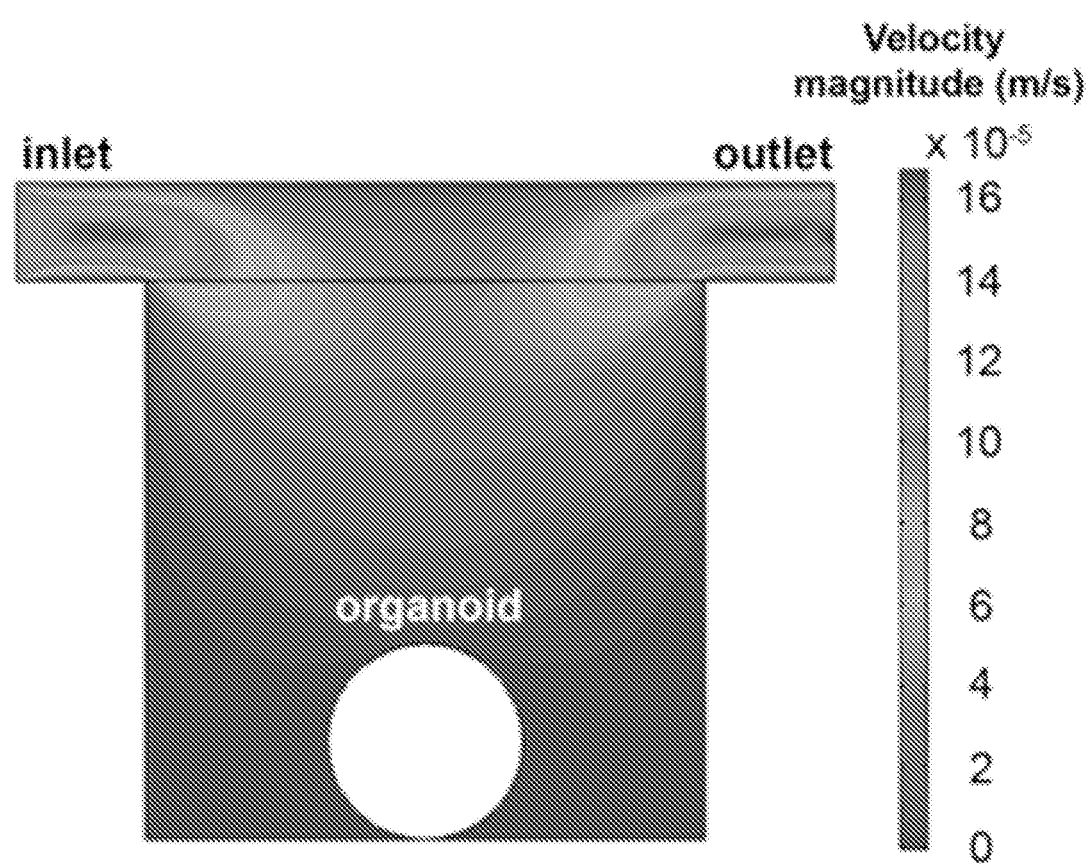
FIG. 13 depicts a velocity profile of a model mesofluidic device, according to an exemplary embodiment of the present invention.

In one experiment, a device was created with the characteristics of the exemplary device depicted in FIG. 2. The device comprised 30 culture chambers. Each culture chamber was cylindrical, having a height and diameter of 5 mm. Connecting each of the 30 culture chambers was a serpentine fluid channel having a dimeter of 700 microns. The device comprised a single fluid inlet at one end of the serpentine fluid channel and a single fluid outlet at the opposite end. The device also comprised fluid delivery cross-channels and fluid removal cross-channels between culture chambers, each cross-channel having a diameter of 200 microns. The fluid channels all entered and exited the culture chambers at one end of the chambers. FIG. 13 is an example velocity profile that demonstrates how the media would enter and exit a culture chamber having fluid channels only at one end of the chambers.

Forebrain organoids were manually loaded into the individual culture chambers using a pipette. Devices were then reversibly sealed along a top surface using a glass slide. One piece of acrylic was positioned about the top surface of the device, and one piece of acrylic was positioned about the bottom surface of the device to allow compression of the device. Both pieces of acrylic were tightened with screws. Live imaging during cell-aggregate culture could be performed directly through the acrylic and glass. The entire device assembly was kept in a standard cell culture incubator during culture, and media was delivered at defined rates or frequencies using a syringe pump.

To first obtain preliminary data about the device design, a two-dimensional (2D) model of the device implementation (excluding cross channels) holding various size organoids was created. COMSOL computational fluid dynamic (CFD) software was used to model laminar flow and mass transport within the device. In all simulations, the 2D steady state solution for the incompressible Navier-Stokes equation was first solved for. This solution was then used in the 2D steady state model of combined convection and diffusion mass transport of a dilute species. Fluid properties were assumed to be those of water. For laminar flow, a no slip boundary condition was assumed at all channel walls. The inlet velocity was calculated based on the volumetric perfusion rate used. The outlet boundary condition was set as an open boundary condition with pressure equal to zero. For mass transport, a no flux boundary condition was assumed at all walls. The initial concentration and inlet concentration of a species was set as the concentration of that species in cell culture media. Finally, to consider the reaction and/or consumption of a given species by an organoid, this was described as the flux of that species through a 2D circular surface, representative of the organoid. Media flow rates ranging from 25-400 µL hr$^{-1}$ and organoid sizes from 0.6 mm to 2.0 mm in diameter were considered in the model.

Conditions within the culture chambers were computer-modeled and compared to a model of the conditions in a miniaturized spinning bioreactor, the SpinΩ. The SpinΩ consists of a 12-well plate modified to include spinning impellers in each well to agitate the media. It is the current state-of-the-art platform for culture of forebrain organoids. Glucose was chosen as a representative species of nutrients to model in each system. Cell consumption and production rates of glucose was obtained from or estimated based on literature. Cell density of a forebrain organoid was modelled at $4.8 \times 10^{14}$ cells m$^{-3}$, according to a value reported in literature.

In a separate set of experimentation, organoids were cultured within device Design Iteration 1, and size and gross morphology were assessed from bright field images acquired at weekly time points. Bright field images of organoids within the manufactured device were compared against a control of forebrain organoids cultured in tissue culture plates in static (non-agitated) media. Organoid size and eccentricity were quantified from images using manual segmentation in ImageJ.

Results from Design Iteration 1

Figure 14:
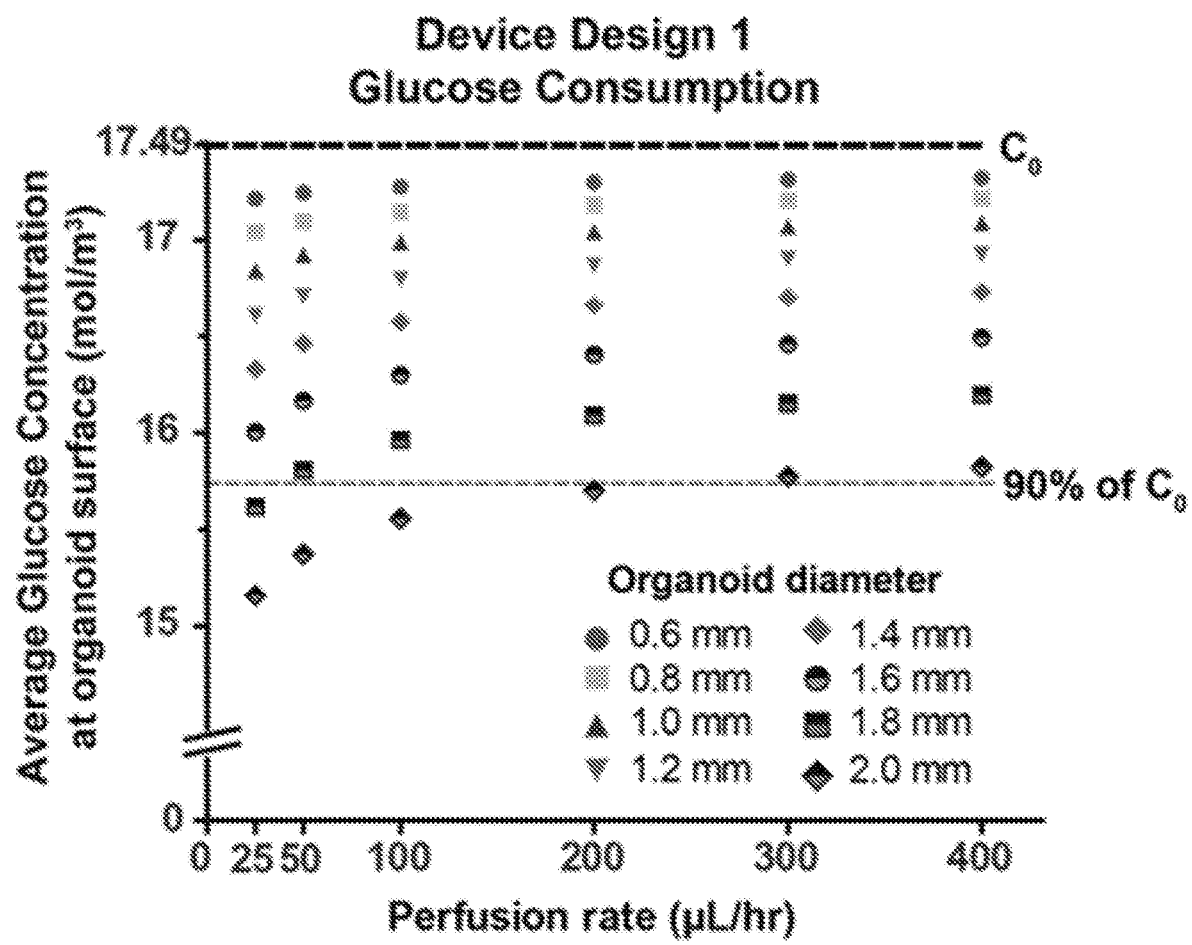
FIG. 14 depicts the results of a glucose transport analysis performed on a computerized model of an exemplary mesofluidic device, according to an exemplary embodiment of the present invention.

Results from the glucose transport and consumption model were obtained. As shown in FIG. 14, which depicts glucose concentrations at organoid surface after a 48-hour period, mesofluidic-device modeling indicates that organoids up to 1.6 mm in diameter experience steady state glucose concentrations within 90% of the initial concentration for all media flow rates modeled. These results indicate that relatively low media perfusion rates can be used for organoids up to 1.8 mm in diameter.

Figure 15:
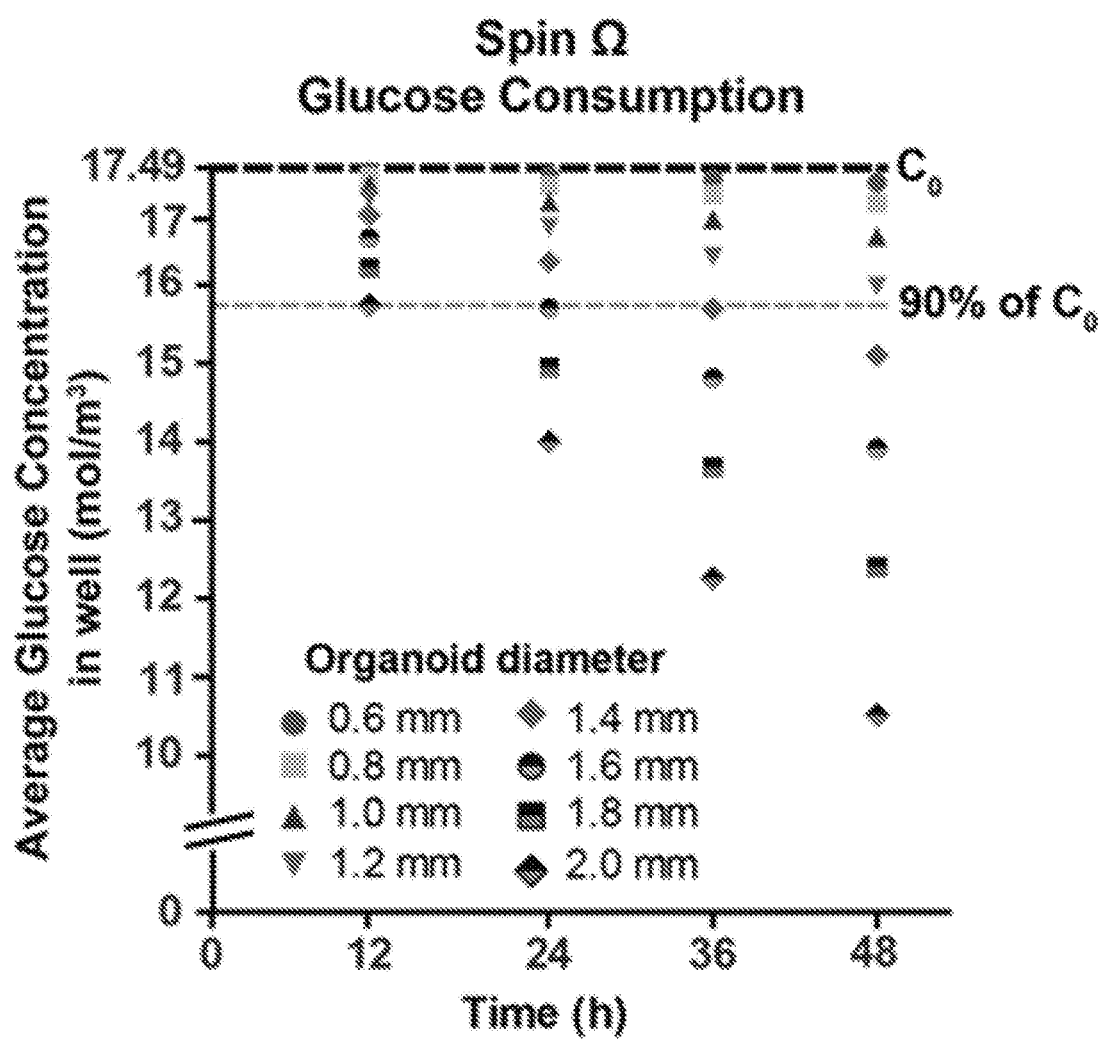
FIG. 15 depicts the results of a glucose transport analysis performed on a computerized model of a spinning bioreactor, according to an exemplary embodiment of the present invention.

For comparison, glucose consumption in the state of the art culture system for forebrain organoids, the SpinΩ bioreactor, was also modeled. The model comprised a single well of a 12-well plate, the single well holding 2 mL of media. For glucose consumption rates, the model assumed there to be 20 organoids in the well. Glucose concentrations at organoid surface after a 48-hour period are depicted in FIG. 15. Calculating the glucose concentration in the SpinΩ over the 48-hour period between media changes showed that the glucose concentration drops below 90% of the initial concentration by 24 hours for organoids that are 1.6 mm in diameter or larger. These modeling results indicate that organoids in the SpinΩ (and likely in similar culture formats) see large variances in glucose concentration between media changes, particularly for organoids 1.6 mm and larger. Remaining within 90% of the initial concentration is therefore perhaps an overly stringent requirement for the microfluidic platform. Additionally, these results suggest that mesofluidic culture has the potential to maintain better consistency in nutrient concentrations over culture periods.

Figure 16:
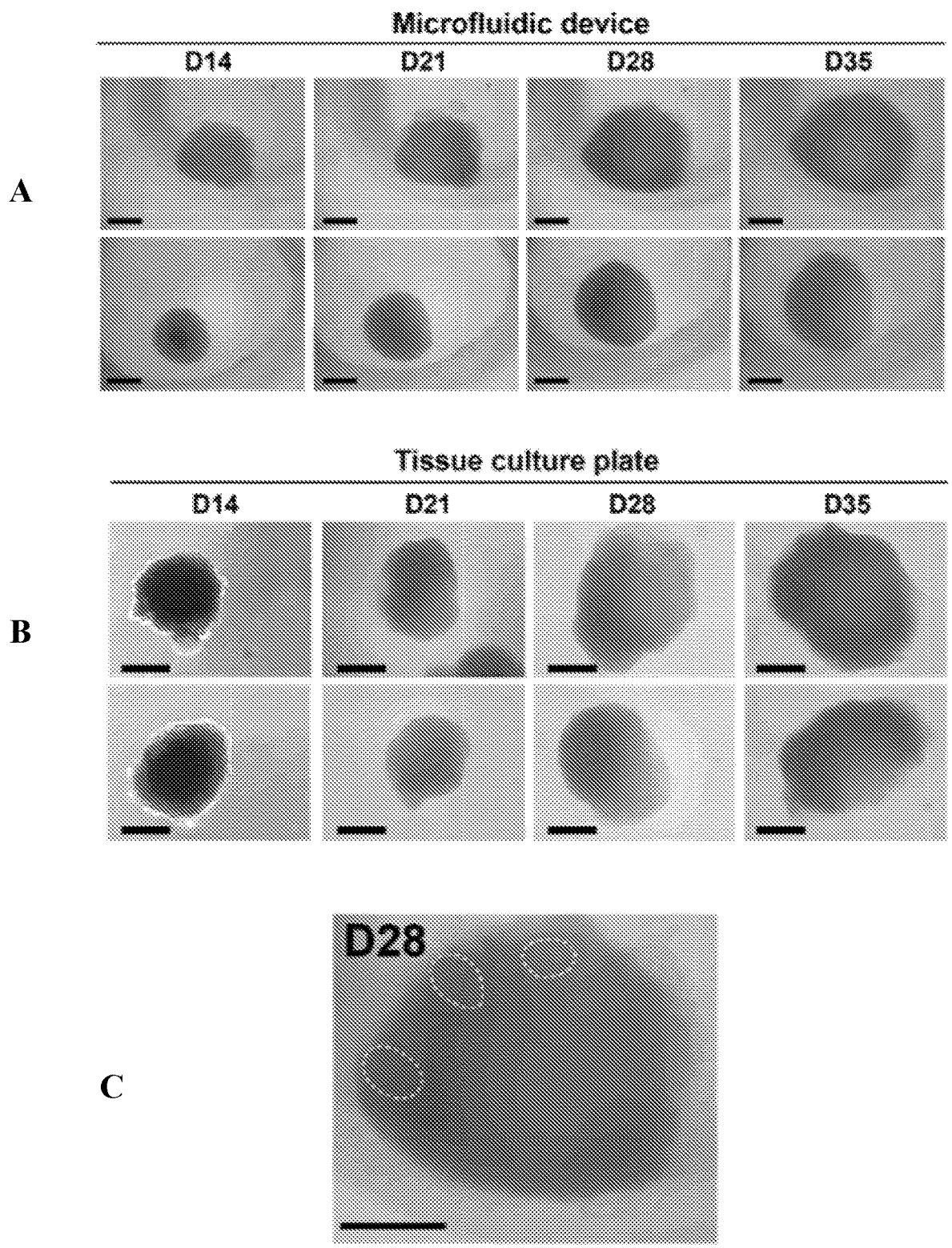
FIG. 16 depicts the results of imaging analysis using an exemplary mesofluidic device and a tissue culture-plate control, according to an exemplary embodiment of the present invention.

Results from bright field imaging were also obtained and compared to the results of organoids cultured in tissue culture plates. To assess organoid development, size and gross morphology were assessed from bright field images acquired at weekly time points. FIG. 16 shows two representative organoids at each time point in mesofluidic devices and different representative organoids at each time point in tissue culture plate controls. A perfusion rate of 200 µL hr$^{-1}$ was chosen for the mesofluidic device. Organoids appeared to grow normally in mesofluidic devices: they displayed expected size increases, maintained a round morphology, and exhibited expected morphological features. In particular, organoids exhibited neural epithelium/neural tube-like structures that are a key feature of forebrain organoids, as seen in FIG. 16C. Heterogeneity was observed in terms of organoid size and morphology both in devices and in tissue culture plate controls.

Figure 17:
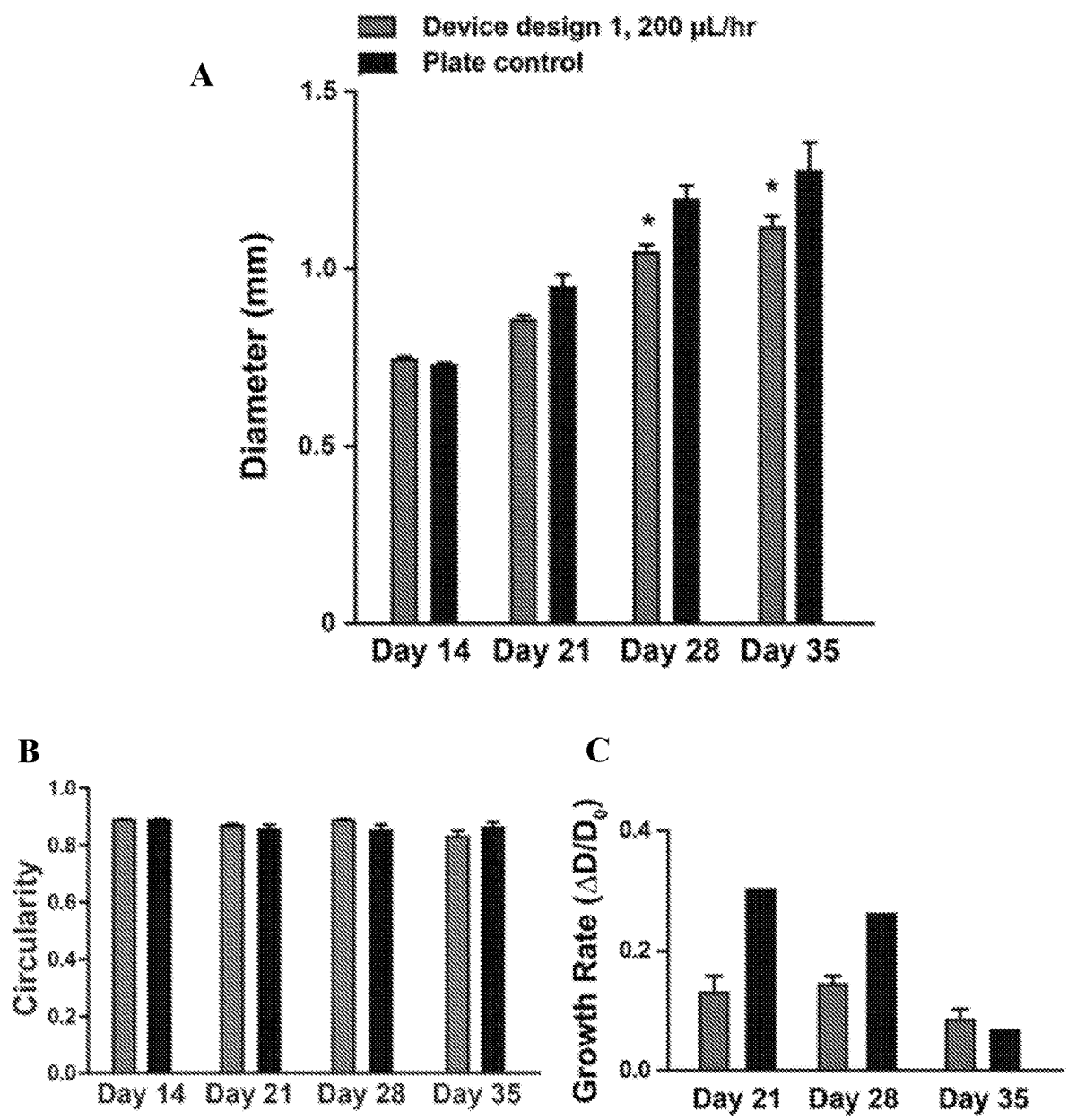
FIG. 17 depicts the results of size and gross morphology testing using an exemplary mesofluidic device, according to an exemplary embodiment of the present invention.

To assess growth, organoid diameter was quantified. The cross-sectional area was measured from bright field images and then used to calculate an equivalent diameter. As shown in FIG. 17A, organoids increased in size over the 35 days of culture. Organoids cultured in devices were, on average, slightly smaller than plate controls at days 21, 28, and 35, although this difference was only statistically significant at days 28 and 35. Organoid circularity was also assessed, with a value of 1 representing a perfect circle, and results are shown in FIG. 17B. Organoids across all conditions tended to be round, and there were no statistically significant differences between days or conditions. Growth rate was also calculated by quantifying the difference in size between two time-points and normalizing by the size at the first of the two time-points, as seen in FIG. 17C. Plate controls showed a higher growth rate at days 21 and 28 compared to organoids cultured in mesofluidic devices, but by day 35 there was little difference in growth rate. Together, based on size, morphology, and growth rate assessments, these results indicated that organoids cultured in devices developed similarly to plate controls, but with some reduction in size and growth.

Conclusions from Design Iteration 1

In Design Iteration 1, it was found that mesofluidic devices as described herein exhibit promising results for culturing cell aggregates. Based on the transport modeling analysis, organoids of greater than 1 mm cultured in mesofluidic devices were likely not nutrient-limited for nutrients such as glucose. This is an improvement over the miniaturized spinning bioreactor. The device also provides benefits over static tissue-plate cultures. Organoids cultured in mesofluidic devices were less heterogeneous and more differentiated than organoids observed in static tissue-plate cultures. Organoids cultured in plates had simpler, less differentiated neural tube structures, particularly at the day 21 time-point.

Methods of Design Iteration 2

Figure 18:
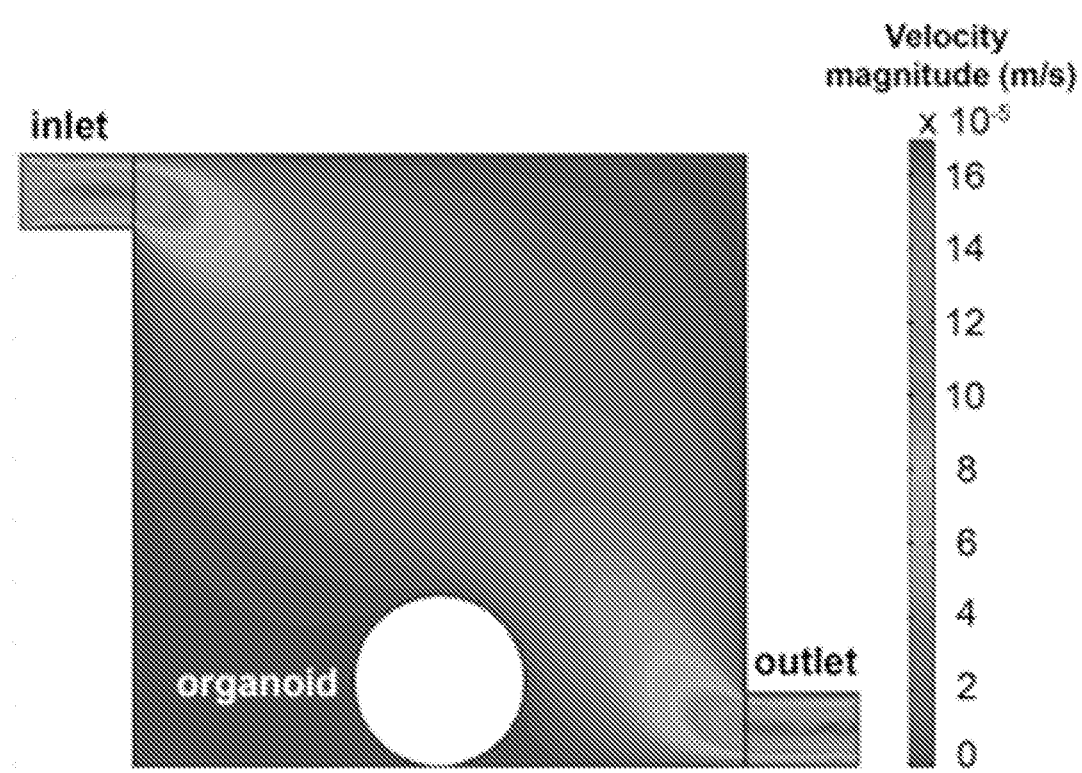
FIG. 18 depicts a velocity profile of a model mesofluidic device, according to an exemplary embodiment of the present invention.

In another experiment, a device was created with the characteristics of the exemplary device depicted in FIG. 7. The device comprised 96 culture chambers, designed to mimic the spacing of a 96-well plate footprint. Each culture chamber had a diameter of 5 mm. The device comprised a top layer and a bottom layer, similar to the depiction found in FIG. 7. On the top layer, each culture chamber connected to a series of fluid channels comprising a diameter of 600 microns. On the bottom layer, each culture chamber connected to a series of fluid channels comprising a diameter of 600 microns. The top layer comprised a single fluid inlet; the bottom layer comprised a single fluid outlet. The two device layers were fabricated from PDMS and bonded together with air plasma treatment prior to experimentation. Organoids were manually loaded into the device via micropipette, and the device was then reversibly sealed with a glass slide using acrylic clamps and screws, as described herein. In Design Iteration 2, no two culture chambers were in fluid communication with each other. FIG. 18 is a velocity profile of a culture chamber in Design Iteration 2, and the figure depicts the flow of media through the chamber.

A 2D computer model, as described in the experiment for Design Iteration 1, was first created for Design Iteration 2. A nutrient consumption model for glucose was compared to that of a miniaturized spinning bioreactor in the same manner as described for Design Iteration 1; however, organoid sizes from 0.6 mm to 2.6 mm in diameter were considered in the second model. Finally, size and gross morphology were assessed from bright field images acquired at weekly time points, and the data was compared to organoids cultured in static tissue-plate cultures in the same manner as described for Design Iteration 1.

Results from Design Iteration 2

Figure 19:
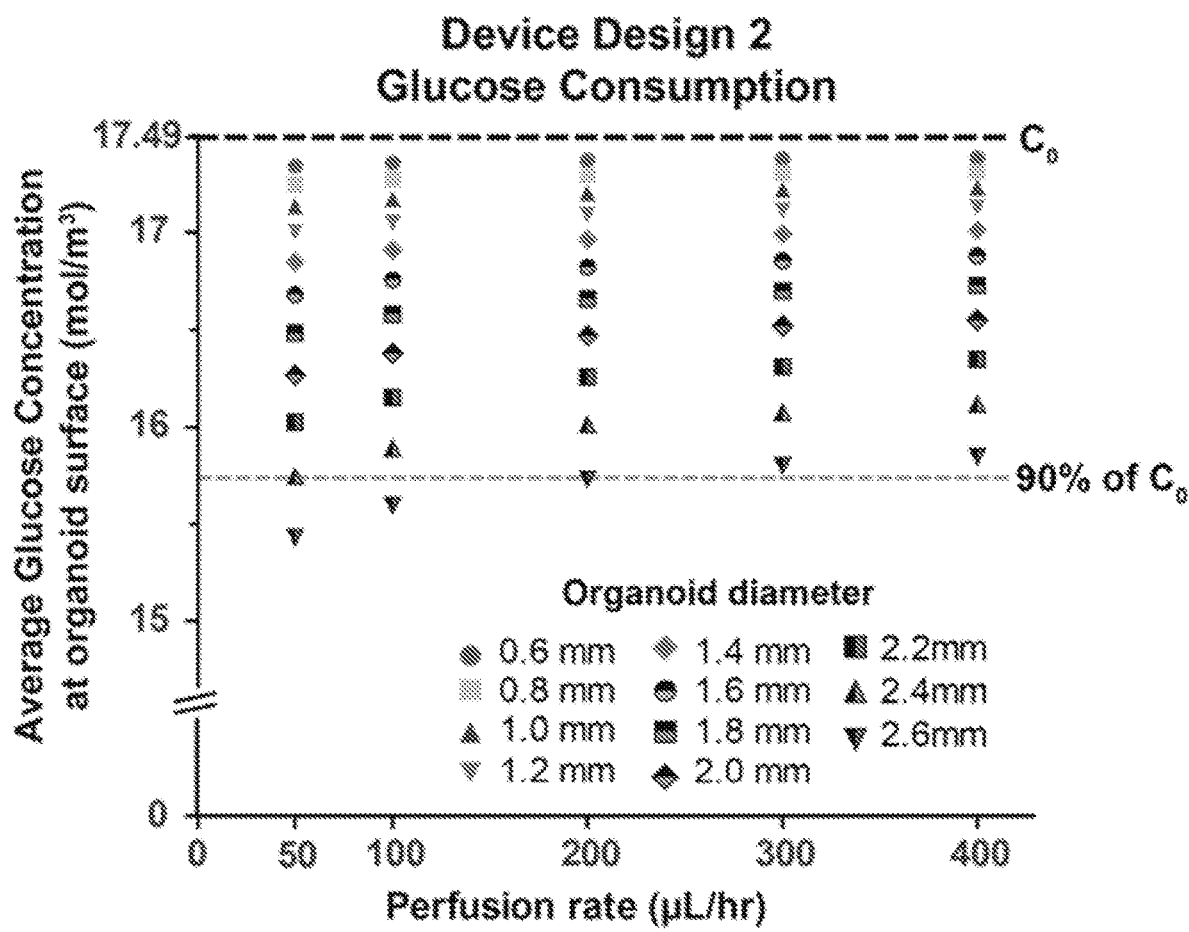
FIG. 19 depicts the results of a glucose transport analysis performed on a computerized model of an exemplary mesofluidic device, according to an exemplary embodiment of the present invention.

Results from the glucose transport and consumption model were obtained. As shown in FIG. 19, which depicts glucose concentrations at organoid surface after a 48-hour period, mesofluidic-device modeling indicates that organoids up to 2.6 mm in diameter experienced glucose concentrations within 90% of the initial concentration. This reflects an improvement over Design Iteration 1, in which media perfusion at 200 $\mu L\ hr^{-1}$ could maintain glucose concentrations within 90% of initial only for organoids of 2.0 mm in diameter and smaller. These results were again compared against the results from the SpinΩ bioreactor model, described above.

Figure 20:
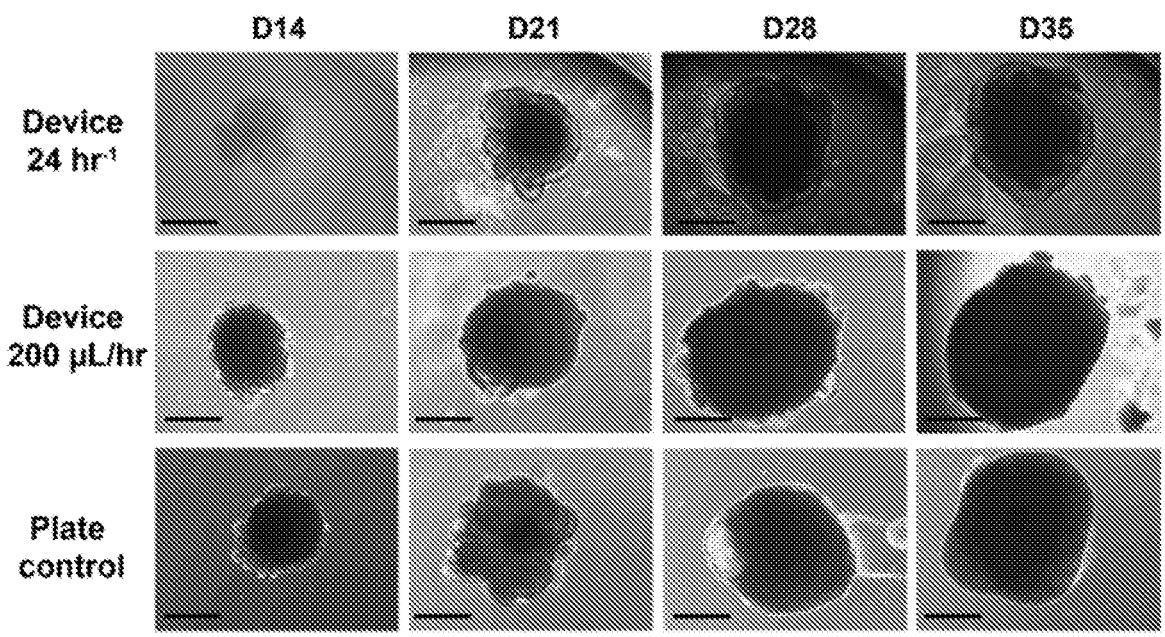
FIG. 20 depicts the results of imaging analysis with two flow rates and a tissue culture-plate control performed using an exemplary mesofluidic device, according to an exemplary embodiment of the present invention.

Results from bright field imaging were also obtained and compared to the results of organoids cultured in tissue culture plates. To assess organoid development, size and gross morphology were assessed from bright field images acquired at weekly time points. FIG. 20 shows representative images of organoids at days 14, 21, 28, and 35 for two mesofluidic-device culture conditions: a first with media exchange every 24 hours (24 $hr^{-1}$), and a second with continuous perfusion at 200 $\mu L\ hr^{-1}$. FIG. 20 also shows static plate controls. The same organoid is shown at each time point in devices, whereas different organoids are shown at each time point for plate controls. Overall, organoids appeared to grow normally in devices with expected size increases, maintenance of round morphologies, and expected morphological features visible. Neural epithelium/neural tube-like structures were observed in organoids cultured in all three conditions, characterized by the round rosette- or bud-like morphology features in the representative images in FIG. 20.

Figure 21:
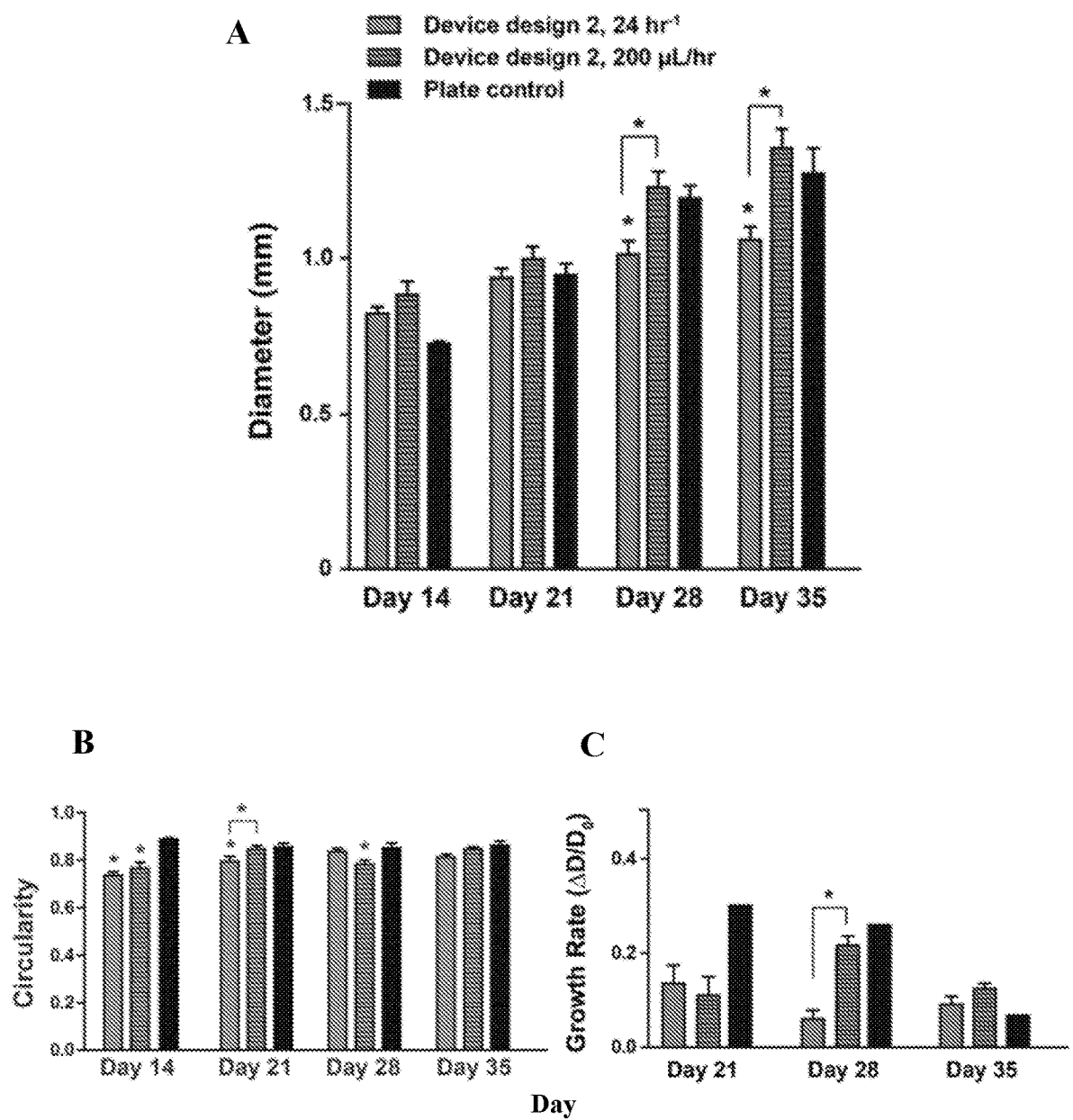
FIG. 21 depicts the results of size and gross morphology testing with two flow rates and a tissue-plate control performed using an exemplary mesofluidic device, according to an exemplary embodiment of the present invention.

Organoid size, circularity, and growth rate for both mesofluidic device conditions and plate controls was also quantified. As shown in FIG. 21A, organoids increased in size over 35 days of culture. Organoids cultured at 200 $\mu L\ hr^{-1}$ were slightly larger in size than plate controls at all time points, but this difference was not statistically significant. In comparison, organoids cultured at 24 $hr^{-1}$ were similar in size to the other conditions at days 14 and 21 but were significantly smaller than 200 $\mu L\ hr^{-1}$ devices and plate controls at days 28 and 35. These results suggest that the 200 $\mu L\ hr^{-1}$ device condition supports growth similar to plate controls. Slightly smaller organoid sizes for the 24 $hr^{-1}$ device-condition may suggest that this media exchange frequency is not sufficient. Organoid circularity was also assessed, and results are shown in FIG. 21B. There were subtle differences in organoid circularity at days 14, 21, and 28, but these differences were not statistically significant by day 35.

Growth rate was also assessed by quantifying the difference in size between two time-points and normalizing by the size at the first of the two time-points, and results are shown in FIG. 21C. Organoids cultured at 200 $\mu L\ hr^{-1}$ had a reduced growth rate compared to plate controls at days 14 and 21 but had a slightly higher growth rate at day 35. Organoids cultured at 24 $hr^{-1}$ had similar growth rates to 200 $\mu L\ hr^{-1}$ devices at days 21 and 35 but, interestingly, had a lower growth rate at day 28. Together, this data suggests that of the two mesofluidic culture conditions tested, continuous perfusion at 200 $\mu L\ hr^{-1}$ may better support organoid growth.

Conclusions from Design Iteration 2

In Design Iteration 2, it was found that mesofluidic devices as described herein exhibit promising results for culturing cell aggregates. Overall, results from this experiment indicate that Design Iteration 2 delivers a nutrient such as glucose more efficiently and that glucose is not likely a limiting nutrient for organoids up to 2.6 mm. This is an improvement over the miniaturized spinning bioreactor, which exhibited large variances in glucose concentration between media changes, particularly for organoids 1.6 mm and larger. The device also provides benefits over static tissue-plate cultures. Organoids cultured in mesofluidic devices with a perfusion rate of 200 μL hr$^{-1}$ had a higher growth rate than plate controls after 35 days of culture.

Methods of Design Iteration 3

Figure 22:
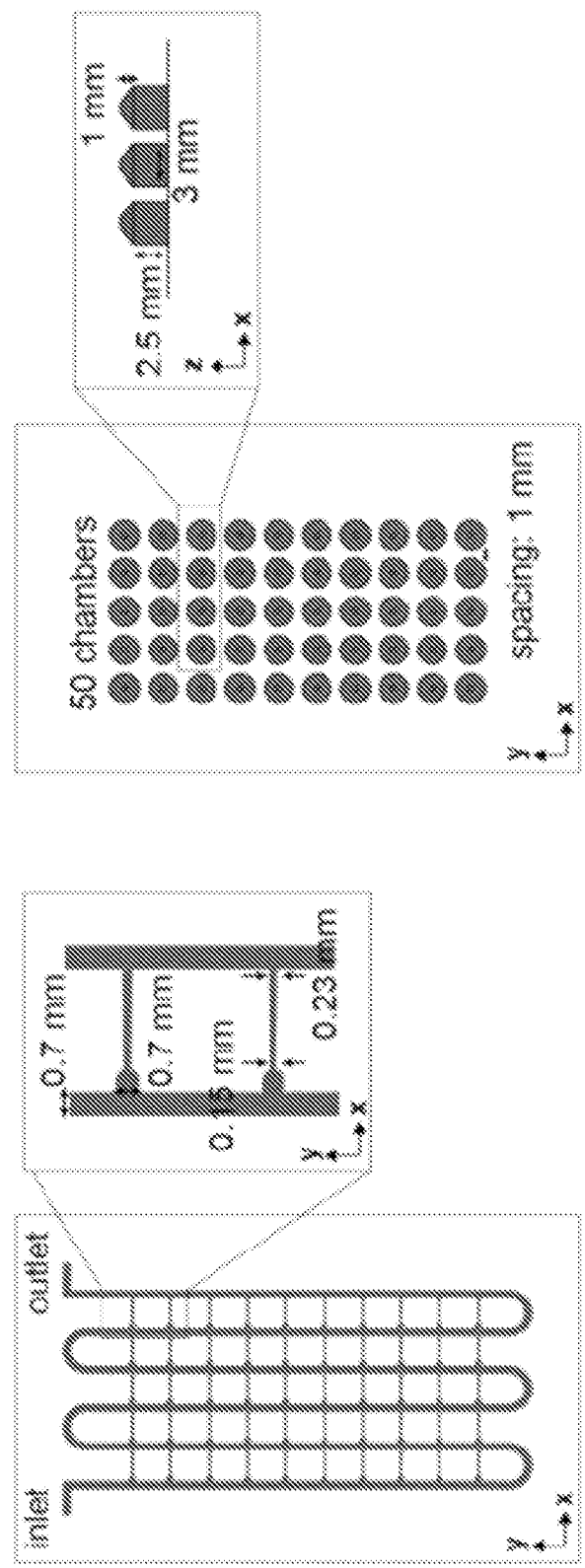
FIG. 22 depicts experimental device dimensions, according to an exemplary embodiment of the present invention.

In another experiment, an aggregate-trap device was created with the characteristics of the exemplary device depicted in FIG. 11. The device comprised a top layer and a bottom layer, similar to the depiction of first trap-plate 1000a and second trap-plate 1000b in FIG. 11. The top layer comprised 50 cell-aggregate traps. These traps were positioned above bottom layer comprising 50 culture chambers. The top layer comprised a single fluid inlet and a single fluid outlet. A serpentine fluid channel flowed from the inlet to the outlet. The fluid channel comprised a diameter of 700 microns. The second trap outlet, or resistance channel, that exited the cell-aggregate-retention grew in diameter: having a dimeter of 150 microns at the connection with the cell-aggregate-retention area and a dimeter of 230 microns at a connection with the fluid channel downstream. This taper design increased fluid flow through the second trap outlet while still prohibiting cell aggregates from flowing through the second trap outlet. The culture chambers on the bottom layer comprised a height of 2.5 mm and a dimeter of 3 mm. The aperture comprised a length of 1 mm and opened into a culture chamber below the trap. The aperture and chamber inlet were integrated into one feature. FIG. 22 depicts the dimensions of the features in Design Iteration 3.

Results from Design Iteration 3

Figure 23:
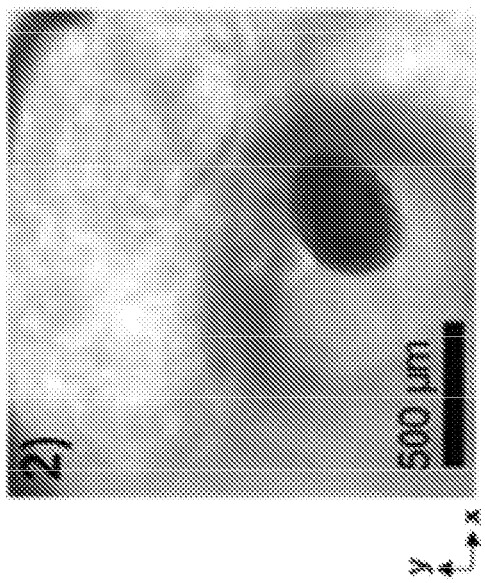
FIG. 23A depicts a cell aggregate suspended in a cell-aggregate-retention area, according to an exemplary embodiment of the present invention.
FIG. 23B depicts a cell aggregate within a culture chamber after falling from a cell-aggregate-retention area, according to an exemplary embodiment of the present invention.
Figure 23:
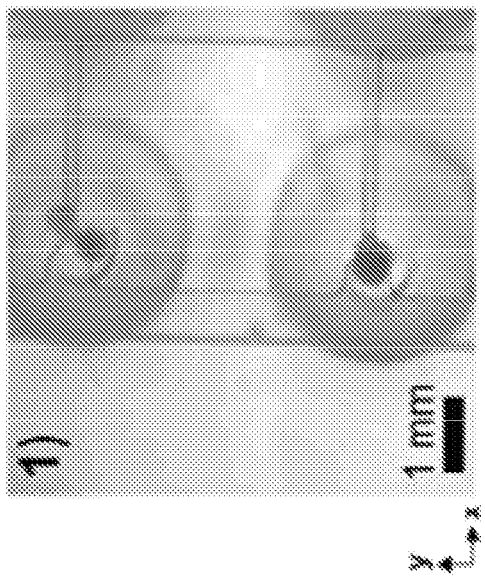

The hydrodynamic loading mechanism in this disclosure was tested on Design Iteration 3. Embryoid bodies (EBs) of comparable size to organoids were suspended in a fluid having a density equal to the density of the EBs. The EB-containing fluid was introduced into devices modeled after Design Iteration 3. Results from the experimentation are found in FIG. 23 It was demonstrated that the cell-aggregate traps effectively trapped and contained EBs in individual cell-aggregate retention areas, as depicted in FIG. 23A. It should be noted that the imaging of the EBs in the figure was performed directly through the device.

A second fluid having a density less than the density of an EB was perfused through the devices. It was demonstrated that an EB can be introduced into a culture chamber by the change in fluid density. The result of the hydrodynamic loading mechanism is depicted in FIG. 23B, where the EB pictured is resting within a culture chamber. It should be noted that the imaging of the EB in the figure was performed directly through the device.

Conclusions from Design Iteration 3

It has been shown that the cell-aggregate-trap devices described in the present disclosure provide substantial benefits for users wishing to culture multiple cell aggregates. It is shown that cell aggregates can be loaded into individual culture chambers by use of a hydrodynamic loading mechanism, thereby eliminating the step of manually injecting the aggregates into individual culture chambers. Additionally, most analysis, including imaging and assays (such as immunohistochemistry, fluorescent in situ hybridization, or tissue clearing), can be performed in the same culture device.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office, other organizations, and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the disclosed technology is defined by the claims appended hereto.

What is claimed is:

1. A non-coplanar culture chamber and cell-aggregate trap system that temporarily traps cell aggregates at a trap level different than a culture level where the cell aggregates are cultured comprising:

a fluid media containing a first cell aggregate and a second cell aggregate, the fluid media having an initial trapping density being equal to or greater than a density of the first cell aggregate and a loading density being less than the density of the first cell aggregate;

a trap mechanism at the trap level that, while the fluid media has the initial trapping density, temporarily traps the first cell aggregate and enables the second cell aggregate to flow downstream from the trap mechanism;

a culture chamber with a culture chamber depth defined by a distance from a top portion of the culture chamber, at the trap level, in proximity to the trap mechanism to a bottom portion of the culture chamber, at the culture level, distal the trap mechanism; and a load mechanism that, while the fluid media has the loading density, utilizes hydrodynamic loading that loads the first cell aggregate in the culture chamber, transferring the temporarily trapped first cell aggregate from the trap level to the culture level where the loaded first cell aggregate is cultured, the culture chamber sized for the hydrodynamic loading of the first cell aggregate; and the trap mechanism comprising:

a trap inlet at the trap level having a diameter greater than a diameter of the first cell aggregate and the second cell aggregate;

a first trap outlet at the trap level having a diameter greater than the diameter of the second cell aggregate;

a second trap outlet at the trap level having a diameter less than the diameter of the first cell aggregate; and a cell-aggregate-retention area at the trap level that temporarily traps the first cell aggregate;

wherein, while the fluid media has the initial trapping density, the non-coplanar culture chamber and cell-aggregate trap system:

temporarily traps the first cell aggregate in the cell-aggregate-retention area at the trap level via fluidic communication between the trap inlet, the cell-aggregate-retention area, and the second trap outlet; and enables the second cell aggregate to flow downstream from the trap mechanism via fluidic communication between the trap inlet and the first trap outlet; and wherein, when the fluid media has the loading density, the hydrodynamic loading loads the trapped first cell aggregate into the culture chamber.

2. A mesofluidic device comprising:

a fluid inlet;

a fluid outlet;

fluid channels; and first and second non-coplanar culture chambers and cell-aggregate trap systems, each of which comprise the non-coplanar culture chamber and cell-aggregate trap system of claim 1, wherein the culture chamber of the first non-coplanar culture chamber and cell-aggregate trap system is a first culture chamber, and wherein the culture chamber of the second non-coplanar culture chamber and cell-aggregate trap system is a second culture chamber;

the first and second culture chambers each comprise:

a chamber inlet in fluid communication with the fluid inlet via at least one of the fluid channels; and a chamber outlet in fluid communication with the fluid outlet via at least one of the fluid channels; and the mesofluidic device retains the first cell aggregate in the first culture chamber, and the second cell aggregate in the second culture chamber.

3. The mesofluidic device of claim 2, wherein the culture chambers are disposed non-coplanar with the fluid channels.

4. The mesofluidic device of claim 2, wherein each of the culture chambers is cylindrical.

5. The non-coplanar culture chamber and cell-aggregate trap system of claim 1, wherein the fluid media at the initial trapping density comprises a first fluid; and wherein the fluid media at the loading density comprises a second fluid different than the first fluid.

6. The non-coplanar culture chamber and cell-aggregate trap system of claim 1, wherein the diameters of both the trap inlet and the first trap outlet are each from 1 mm to 7 mm.

7. The non-coplanar culture chamber and cell-aggregate trap system of claim 1, wherein the diameters of both the trap inlet and the first trap outlet are each from 2 mm to 5 mm.

* * * * *